United States Patent
Srinivasan et al.

(10) Patent No.: US 11,434,256 B2
(45) Date of Patent: Sep. 6, 2022

(54) PROCESS FOR THE PREPARATION OF 3α,7α-DIHYDROXY-6α-ETHYL-5β-CHOLAN-24-OIC ACID

(71) Applicant: MSN LABORATORIES PRIVATE LIMITED, R&D CENTER, Telangana (IN)

(72) Inventors: Thirumalai Rajan Srinivasan, Hyderabad (IN); Eswaraiah Sajja, Hyderabad (IN); Venkata Panakala Rao Gogulapati, Hyderabad (IN); Ganapathi Chary Nagunuri, Hyderabad (IN)

(73) Assignee: MSN LABORATORIES PRIVATE LIMITED, R&D CENTER, Telangana (IN)

( * ) Notice: Subject to any disclaimer, the term of this patent is extended or adjusted under 35 U.S.C. 154(b) by 0 days.

(21) Appl. No.: 16/965,243

(22) PCT Filed: Jan. 25, 2019

(86) PCT No.: PCT/IN2019/050059
§ 371 (c)(1),
(2) Date: Jul. 27, 2020

(87) PCT Pub. No.: WO2019/145977
PCT Pub. Date: Aug. 1, 2019

(65) Prior Publication Data
US 2020/0369713 A1    Nov. 26, 2020

(30) Foreign Application Priority Data

Jan. 25, 2018 (IN) .............................. 201810003053
Nov. 28, 2018 (IN) .............................. 201841044858

(51) Int. Cl.
*C07J 9/00*    (2006.01)

(52) U.S. Cl.
CPC ........... *C07J 9/005* (2013.01); *C07B 2200/13* (2013.01)

(58) Field of Classification Search
CPC ...................................................... C07J 9/005
See application file for complete search history.

(56) References Cited

FOREIGN PATENT DOCUMENTS

WO    WO 2013192097 A1    12/2013
WO    WO 2016045480 A1    3/2016
(Continued)

OTHER PUBLICATIONS

Markham and Keam (Drugs (2016) 76:1221-1226). (Year: 2016).*
(Continued)

*Primary Examiner* — Benjamin J Packard
(74) *Attorney, Agent, or Firm* — IP Pundit LLC

(57) ABSTRACT

The present invention relates to an improved process for the preparation of 3α,7α-dihydroxy6α-ethyl-5β-cholan-24-oic acid compound of formula-1, represented by the following structural formula: Formula-1 The present invention also relates to process for the preparation of ethylene diamine
(Continued)

and tertiary butyl amine salts of 3α,7α-dihydroxy6α-ethyl-5β-cholan-24-oic acid which are useful in the preparation of pure 3α,7α-dihydroxy6α-ethyl-5β-cholan-24-oic acid.

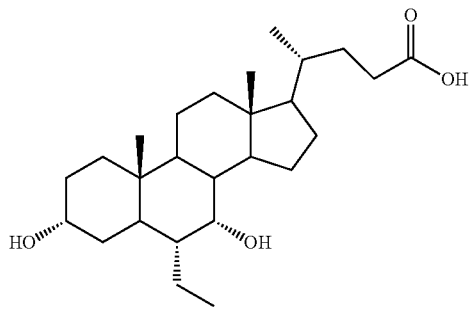

(I)

7 Claims, 1 Drawing Sheet

(56) References Cited

FOREIGN PATENT DOCUMENTS

| WO | WO 2017137931 A1 | 8/2017 |
| WO | WO 2017174515 A1 | 10/2017 |
| WO | WO 2018010651 A1 | 1/2018 |

OTHER PUBLICATIONS

Search Steategy dated Aug. 1, 2019 in the file history of the corresponding international application.
International Search Report dated Aug. 1, 2019.
Written Opinion of the International Searching Authority dated Aug. 1, 2019.

* cited by examiner

PROCESS FOR THE PREPARATION OF 3α,7α-DIHYDROXY-6α-ETHYL-5β-CHOLAN-24-OIC ACID

RELATED APPLICATIONS

This application claims the benefit of priority of our Indian patent application numbers 201841003053 filed on 25 Jan. 2018 and 201841044858 filed on 28 Nov. 2018 which is incorporated herein by reference.

FIELD OF THE INVENTION

The present invention relates to an improved process for the preparation of 3α,7α-dihydroxy-6α-ethyl-5β-cholan-24-oic acid compound of formula-1, represented by the following structural formula:

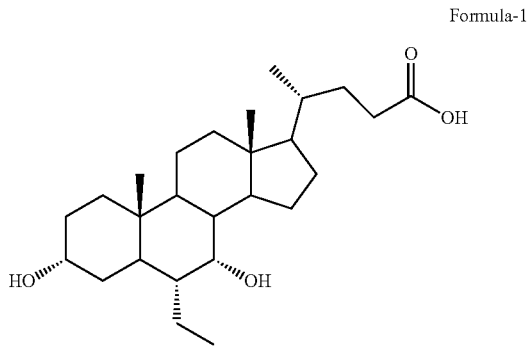 [SMILES: CC[C@@H]1C2C[C@H](O)CC[C@]2(C)C2CC[C@@]3(C)C(CCC3[C@H](C)CCC(=O)O)C2[C@@H]1O]

Formula-1

The present invention also relates to ethylene diamine salt of 3α,7α-dihydroxy-6α-ethyl-5β-cholan-24-oic acid which is useful in the preparation of pure 3α,7α-dihydroxy-6α-ethyl-5β-cholan-24-oic acid.

The present invention relates to 3α,7α-dihydroxy-6α-ethyl-5β-cholan-24-oic acid tertiary butyl amine salt, which is referred as Obeticholic acid tertiary butyl amine salt and the same has been represented by the following structural formula.

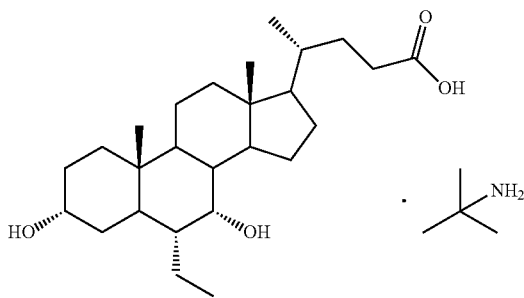

and process for its preparation thereof.

The present invention also relates to process for the preparation of amorphous Obeticholic acid.

Further, the present invention provides use of Obeticholic acid tertiary butyl amine salt in the preparation of pure Obeticholic acid.

BACKGROUND OF THE INVENTION

Obeticholic acid (OCALIVA) is chemically known as 3α,7α-dihydroxy-6α-ethyl-5β-cholan-24-oic acid is a farnesoid X receptor (FXR) agonist, is indicated for the treatment of primary biliary cholangitis (PBC) in combination with ursodeoxycholic acid (UDCA) in adults with an inadequate response to UDCA, or as monotherapy in adults unable to tolerate UDCA. Obeticholic acid was approved by USFDA in May, 2016.

Obeticholic acid has been approved by European Commission for the treatment of primary biliary cirrhosis.

U.S. Pat. No. 7,138,390 first discloses Obeticholic acid and the process for its preparation.

International (PCT) Publication No. WO/2013/192097 A1 discloses various crystalline polymorphic Form-A, Form-C, Form-D, Form-G, Form-F, Form-I and amorphous form of Obeticholic acid.

BRIEF DESCRIPTION OF THE INVENTION

First embodiment of the present invention relates to Obeticholic acid ethylene diamine salt compound of formula-1a and process for its preparation.

Second embodiment of the present invention provides process for the purification of 3α-hydroxy-6-ethylidene-7-keto-5β-cholan-24-oic acid.

Third embodiment of the present invention provides an improved process for the preparation of Obeticholic acid.

Fourth embodiment of the present invention provides an alternative process for the preparation of Obeticholic acid.

Fifth embodiment of the present invention provides a novel process for the preparation of Obeticholic acid.

Sixth embodiment of the present invention provides a novel process for the preparation of Obeticholic acid.

Seventh embodiment of the present invention provides a novel process for the preparation of Obeticholic acid.

Eighth embodiment of the present invention provides a process for the preparation of Obeticholic acid.

Ninth embodiment of the present invention relates to novel intermediate compounds which are useful in the preparation of Obeticholic acid.

Tenth embodiment of the present invention provides an improved process for the preparation of 3α,7α-di-trimethylsililoxy-5β-cholanate.

Eleventh embodiment of the present invention provides crystalline form of Obeticholic acid tertiary butyl amine salt.

Twelfth embodiment of the present invention provides a crystalline form of Obeticholic acid tertiary butyl amine salt herein after designated as form-M.

Thirteenth embodiment of the present invention provides a process for the preparation of crystalline form of Obeticholic acid tertiary butyl amine salt.

Fourteenth embodiment of the present invention provides a process for the preparation of amorphous Obeticholic acid.

Fifteenth embodiment of the present invention provides a process for the preparation of Obeticholic acid.

BRIEF DESCRIPTION OF THE DRAWINGS

FIG. 1: Illustrates the PXRD pattern of amorphous form of Obeticholic acid ethylene diamine salt compound of formula-1a.

DETAILED DESCRIPTION OF THE INVENTION

Figure 1:
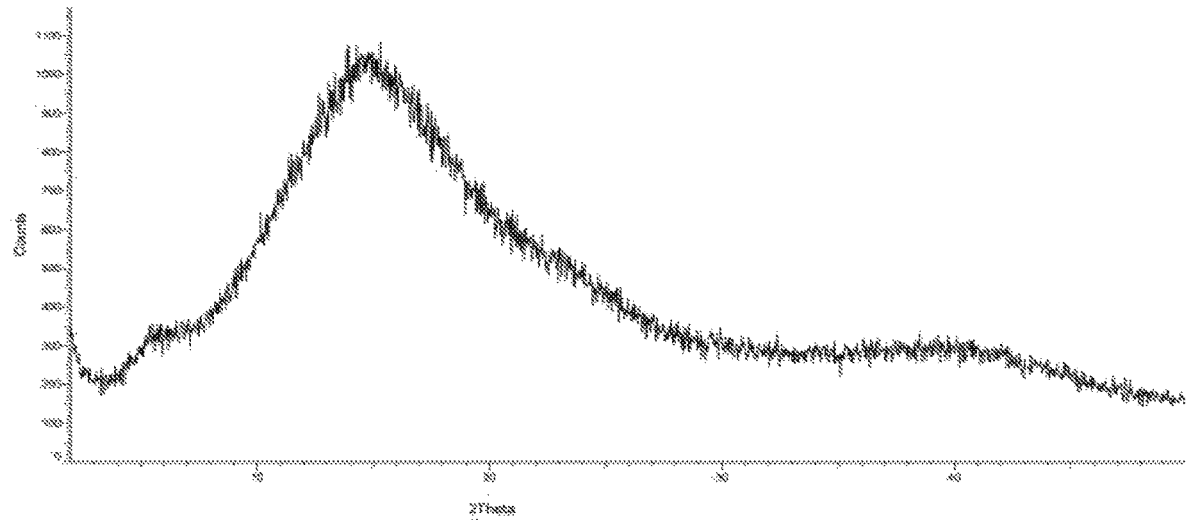

As used herein the term "suitable solvent" used in the present invention refers to "hydrocarbon solvents" such as n-hexane, n-heptane, cyclohexane, pet ether, toluene, pentane, cycloheptane, methylcyclohexane, m-, o-, or p-xylene, and the like; "ether solvents" such as dimethoxy methane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethylacetamide (DMA), dimethylformamide (DMF), dimethyl sulfoxide (DMSO), N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, propylene glycol, 2-methoxyethanol, 1,2-ethoxyethanol, diethylene glycol, 1, 2, or 3-pentanol, neo-pentyl alcohol, t-pentyl alcohol, diethylene glycol monoethyl ether, cyclohexanol, anisole, benzyl alcohol, phenol, or glycerol and the like; "polar solvents" such as water or mixtures thereof.

The term "suitable base" used herein the present invention until unless specified is selected from inorganic bases like "alkali metal hydroxides" such as lithium hydroxide, sodium hydroxide, potassium hydroxide and the like; "alkali metal carbonates" such as sodium carbonate, potassium carbonate, lithium carbonate and the like; "alkali metal bicarbonates" such as sodium bicarbonate, potassium bicarbonate, lithium bicarbonate and the like; "alkali metal hydrides" such as potassium hydride, lithium hydride and the like; ammonia; and organic bases such "alkali metal alkoxides" such as sodium methoxide, sodium ethoxide, sodium tert-butoxide, potassium methoxide, potassium ethoxide, potassium tert-butoxide and the like; triethyl amine, methyl amine, ethyl amine, 1,8-diazabicyclo[5.4.0]undec-7-ene (DBU), 1,5 -diazabicyclo(4.3.0)non-5 -ene (DBN), lithium dioisopropyl amide (LDA), n-butyl lithium, tribenzylamine, isopropyl amine, diisopropyl amine, diiso propylethylamine, N-methylmorpholine, N-ethylmorpholine, piperidine, dimethylamino pyridine, morpholine, pyridine, 2,6-lutidine, 2,4,6-collidine, imidazole, 1-methyl imidazole, 1,2,4-triazole, 1,4-diazabicyclo[2.2.2]octane (DABCO) or mixtures thereof.

First embodiment of the present invention provides Obeticholic acid ethylene diamine salt compound of formula-1a.

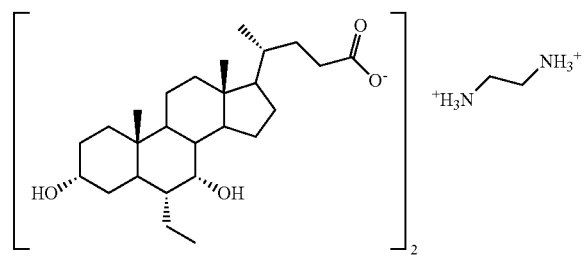

Formula-1a

In the first embodiment, the present invention provides solid state forms of Obeticholic acid ethylene diamine salt compound of formula-1a.

In the first embodiment, the present invention provides a process for the preparation of Obeticholic acid ethylene diamine salt compound of formula-1a, comprising:

a) Adding ethylene diamine and a suitable solvent to Obeticholic acid, b) isolating Obeticholic acid ethylene diamine salt compound of formula-1a.

In an embodiment of the present invention wherein, the suitable solvent used in step-a) is selected from chloro solvents, acetic acid, alcohol solvents, ketone solvents, polar solvents, hydrocarbon solvents, nitrile solvents, ether solvents, ester solvents, polar-aprotic solvents or their mixtures thereof.

In an embodiment of the present invention, isolating the Obeticholic acid ethylene diamine salt is carried out by any methods known in the art or is isolated by employing any of the techniques, but not limited to: decantation, filtration by gravity or suction, centrifugation, adding solvent to make slurry followed by filtration, or other techniques specific to the equipment used and the like, and optionally washing with a solvent.

In an embodiment of the present invention the above compound of formula-1a useful in the preparation of pure Obeticholic acid.

In an embodiment of the present the compound of formula-1a can be converted into Obeticholic acid by treating with a suitable acid selected from inorganic acids like hydrochloric acid, hydrobromic acid, sulfuric acid, nitric acid, phosphoric acid and organic acids like oxalic acid, maleic acid, malonic acid, tartaric acid, fumaric acid, citric acid, malic acid, succinic acid, mandelic acid, lactic acid, acetic acid, propionic acid, 2-chloromandelate, p-toluene sulfonic acid, ethane-1,2-disulfonic acid, camphor sulfonic acid, ethane sulfonic acid, methane sulfonic acid, naphthalene-2-sulfonic acid, benzene sulfonic acid, adipic acid, glutaric acid, glutamic acid, palmitic acid or aspartic acid.

Second embodiment of the present invention provides a process for the purification of 3α-hydroxy-6-ethylidene-7-keto-5β-cholan-24-oic acid, comprising dissolving 3α-hydroxy-6-ethylidene-7-keto-5β-cholan-24-oic acid in a suitable solvent and isolating pure 3α-hydroxy-6-ethylidene-7-keto-5β-cholan-24-oic acid.

In the second embodiment the suitable solvent used is selected from chloro solvents, alcohol solvents, polar solvents, hydrocarbon solvents, nitrile solvents, ether solvents, ester solvents, polar-aprotic solvents or their mixtures; preferably ketone solvents;

In the second embodiment, of the present invention heating a solution of 3α-hydroxy-6-ethylidene-7-keto-5β-cholan-24-oic acid to a temperature ranging from 30° C. to reflux temperature of the solvent used.

In the second embodiment of the present invention isolating 3α-hydroxy-6-ethylidene-7-keto-5β-cholan-24-oic acid is carried out by any methods known in the art or is isolated by employing any of the techniques, but not limited to: decantation, filtration by gravity or suction, centrifugation, adding solvent to make slurry followed by filtration, or other techniques specific to the equipment used and the like, and optionally washing with a solvent.

Third embodiment of the present invention provides an improved process for the preparation of Obeticholic acid.

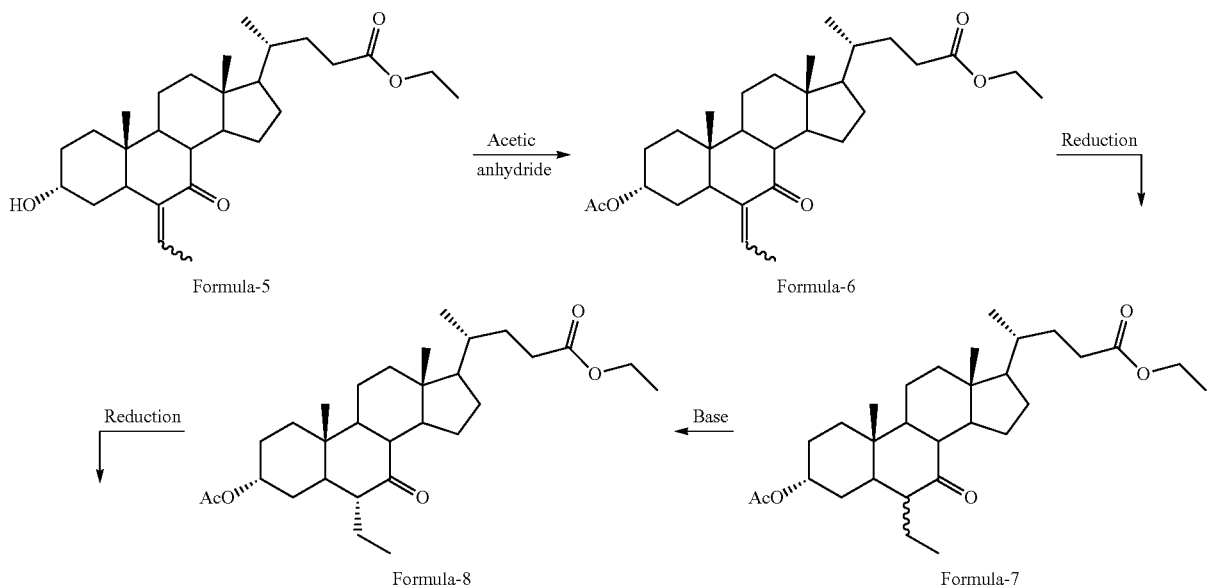

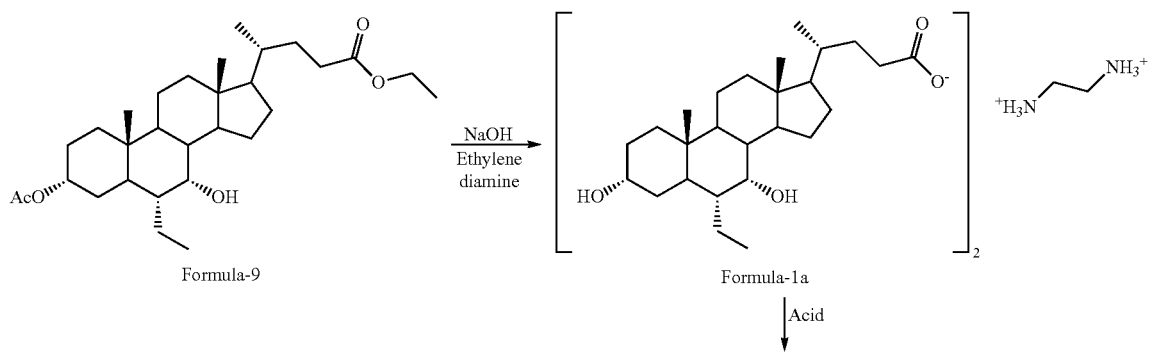

Formula-1
(Obeticholic acid)

Fourth embodiment of the present invention provides an alternative process for the preparation of Obeticholic acid, comprising:

a) Treating ethyl 3α-hydroxy-6-ethylidene-7-keto-5β-cholan-24-oate compound of formula-5 with propionic anhydride in the presence of a suitable base in a suitable solvent ethyl 3α-propionyloxy-6-ethylidene-7-keto-5β-cholan-24-oate compound of formula-10, b) reducing the compound of formula-10 with a suitable reducing agent in a suitable solvent to provide ethyl 3α-propionyloxy-6-ethyl-7-keto-5β-cholan-24-oate compound of formula-11, c) treating the compound of formula-11 with a suitable base in a suitable solvent to provide ethyl 3α-propionyloxy-6α-ethyl-7-keto-5β-cholan-24-oate compound of formula-12, d) reducing the compound of formula-12 with a suitable reducing agent in a suitable solvent to provide ethyl 3α-propionyloxy-6α-ethyl-7a-hydroxy-5β-cholan-24-oate compound of formula-13, e) treating the compound of formula-13 with a suitable base in a suitable solvent to provide Obeticholic acid, f) treating Obeticholic acid with ethylene diamine in a suitable solvent to provide Obeticholic acid ethylene diamine salt compound of formula-1a, g) optionally purifying the compound of formula-1a with a suitable solvent, h) treating the compound of formula-1a with a suitable acid in a suitable solvent to provide Obeticholic acid.

In an embodiment, the process of the present invention is schematically illustrated as below:

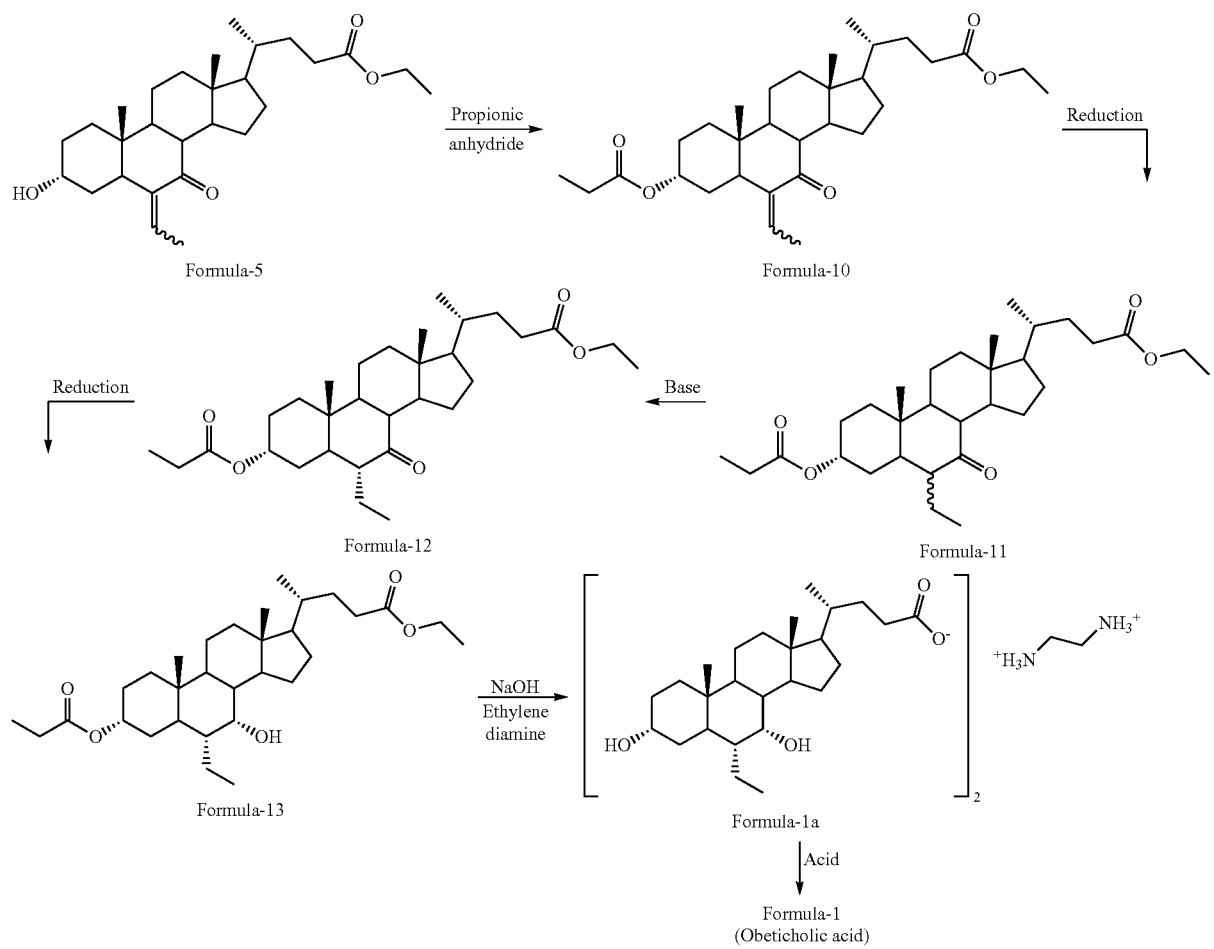

Fifth embodiment of the present invention provides a novel process for the preparation of Obeticholic acid, comprising:

a) Reacting methyl 3α-hydroxy-6-ethylidene-7-keto-5β-cholan-24-oate compound of formula-14 with propionic anhydride in the presence of a suitable base and in a suitable catalyst in a suitable solvent to provide methyl 3α-propionyloxy-6-ethylidene-7-keto-5β-cholan-24-oate compound of formula-15 b) reducing the compound of formula-15 with a suitable reducing agent in a suitable solvent to provide methyl 3α-propionyloxy-6-ethyl-7-keto-5β-cholan-24-oate compound of formula-16, c) treating the compound of formula-16 with a suitable base in a suitable solvent to provide methyl 3α-propionyloxy-6α-ethyl-7-keto-5β-cholan-24-oate compound of formula-17, d) reducing the compound of formula-17 with a suitable reducing agent in a suitable solvent to provide methyl 3α-propionyloxy-6α-ethyl-7α-hydroxy-5β-cholan-24-oate compound of formula-18, e) treating the compound of formula-18 with a suitable base in a suitable solvent to provide Obeticholic acid compound of formula-1, f) treating the compound of formula-1 with ethylene diamine in a suitable solvent to provide Obeticholic acid ethylene diamine salt compound of formula-1a, g) optionally purifying the compound of formula-1a with a suitable solvent, h) treating the compound of formula-1a with a suitable acid in a suitable solvent to provide Obeticholic acid compound of formula-1.

In the process of the fifth embodiment, the suitable reducing agent used in step-b) is selected from transition metal catalyst such as copper, nickel, palladium, platinum, rhodium, iridium, and ruthenium in presence of hydrogen gas pressure; the suitable base used in step-a), c) and e) is selected from organic or inorganic base; the suitable reducing agent used in step-d) is selected from sodium borohydride, potassium borohydride, sodium cyanoboro hydride, tetramethylammonium borohydride, sodium triacetoxyborohydride; the suitable solvent used in step-a) to step-h) is selected from chloro solvents, alcohol solvents, ester solvents, ketone solvents, nitrile solvents, ether solvents, polar aprotic solvents, hydrocarbon solvents and polar solvents like water or mixture thereof.

In an embodiment, the process of the present invention is schematically represented as follows:

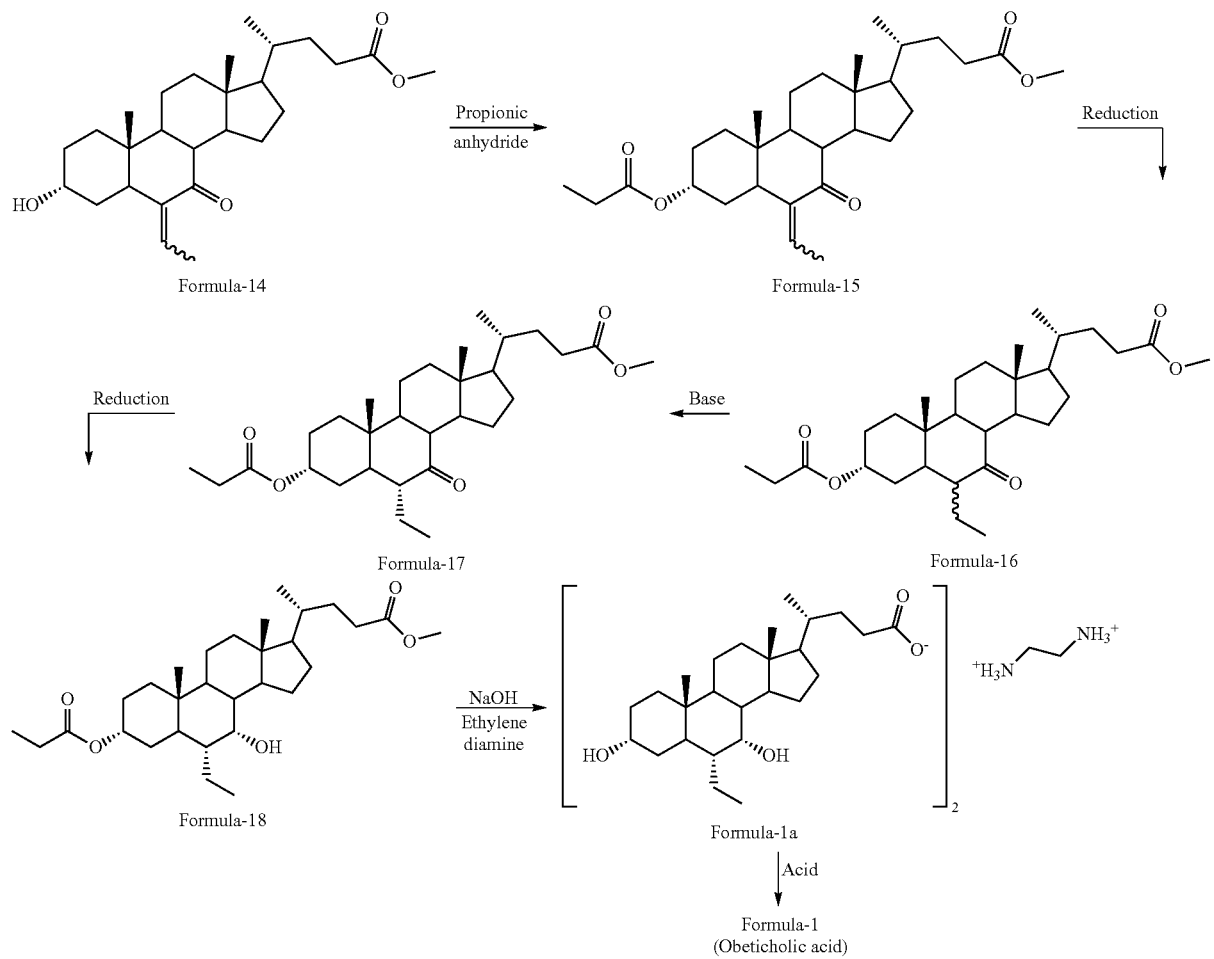

Sixth embodiment of the present invention provides a novel process for the preparation of Obeticholic acid, comprising:
a) Reacting ethyl 3α-hydroxy-6-ethylidene-7-keto-5β-cholan-24-oate compound of formula-5 with methoxy methyl chloride in a suitable solvent to provide ethyl 3α-methoxymethoxy-6-ethylidene-7-keto-5β-cholan-24-oate compound of formula-19,
b) reducing the compound of formula-19 with a suitable reducing agent to provide ethyl 3α-methoxymethoxy-6-ethyl-7-keto-5β-cholan-24-oate compound of formula-20,
c) treating the compound of formula-20 with a suitable base in a suitable solvent to provide ethyl 3α-methoxymethoxy-6α-ethyl-7-keto-5β-cholan-24-oate compound of formula-21,
d) converting the compound of formula-21 to Obeticholic acid.

In the sixth embodiment, the process of the present invention is schematically represented as follows:

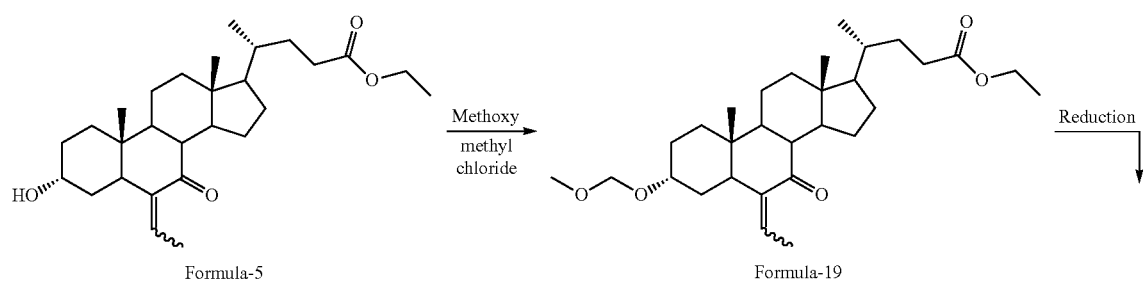

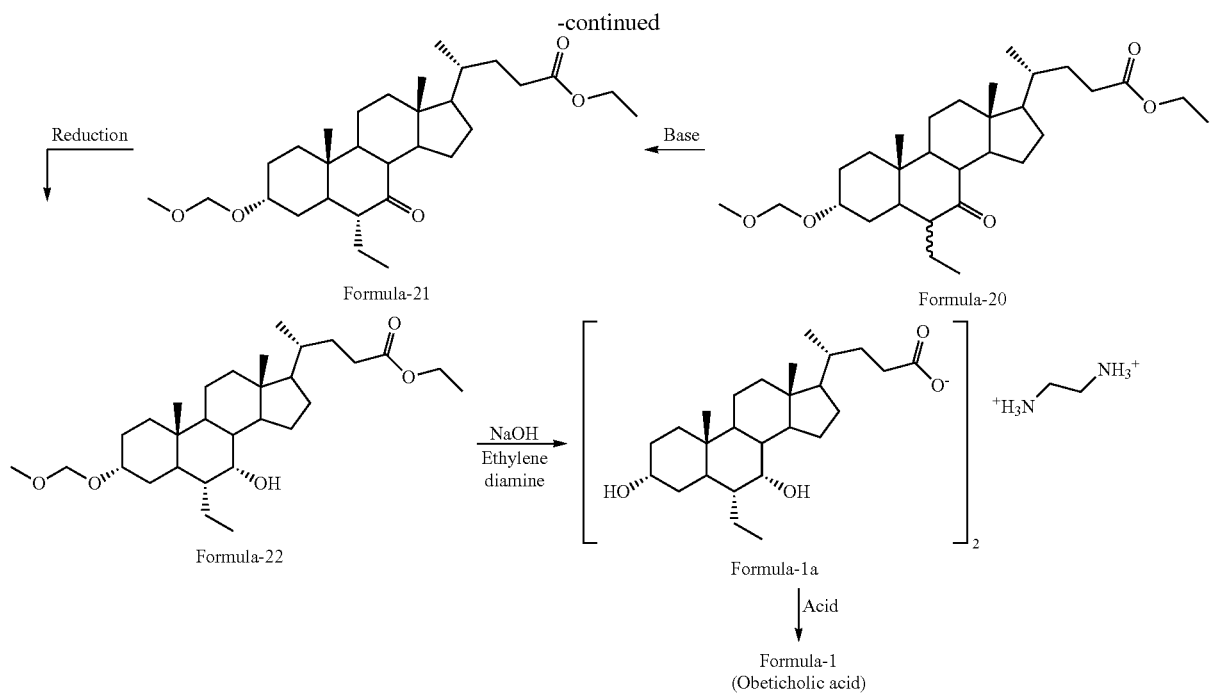

Seventh embodiment of the present invention provides a novel process for the preparation of Obeticholic acid, comprising:
a) Reacting alkyl 3,7-diketo-cholanate compound of formula-23 with ethylene glycol in the presence of a suitable acid in a suitable solvent to provide compound of formula-24,
b) Reacting the compound of formula-24 with trimethyl silyl chloride in the presence of a suitable base in a suitable solvent to provide compound of formula-25,
c) Reacting the compound of formula-25 with acetaldehyde in the presence of BF3-etherate to provide compound of formula-26,
d) Converting the compound of formula-26 to Obeticholic acid.

In the seventh embodiment, the process of the present invention is schematically represented as follows:

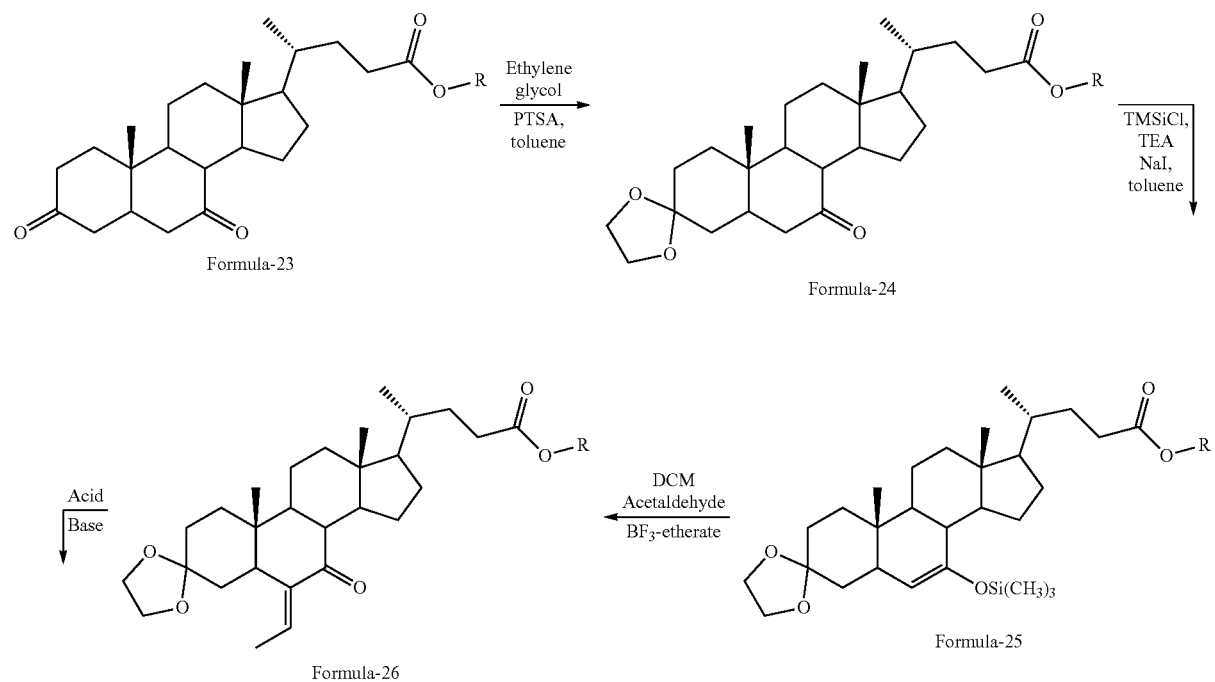

13
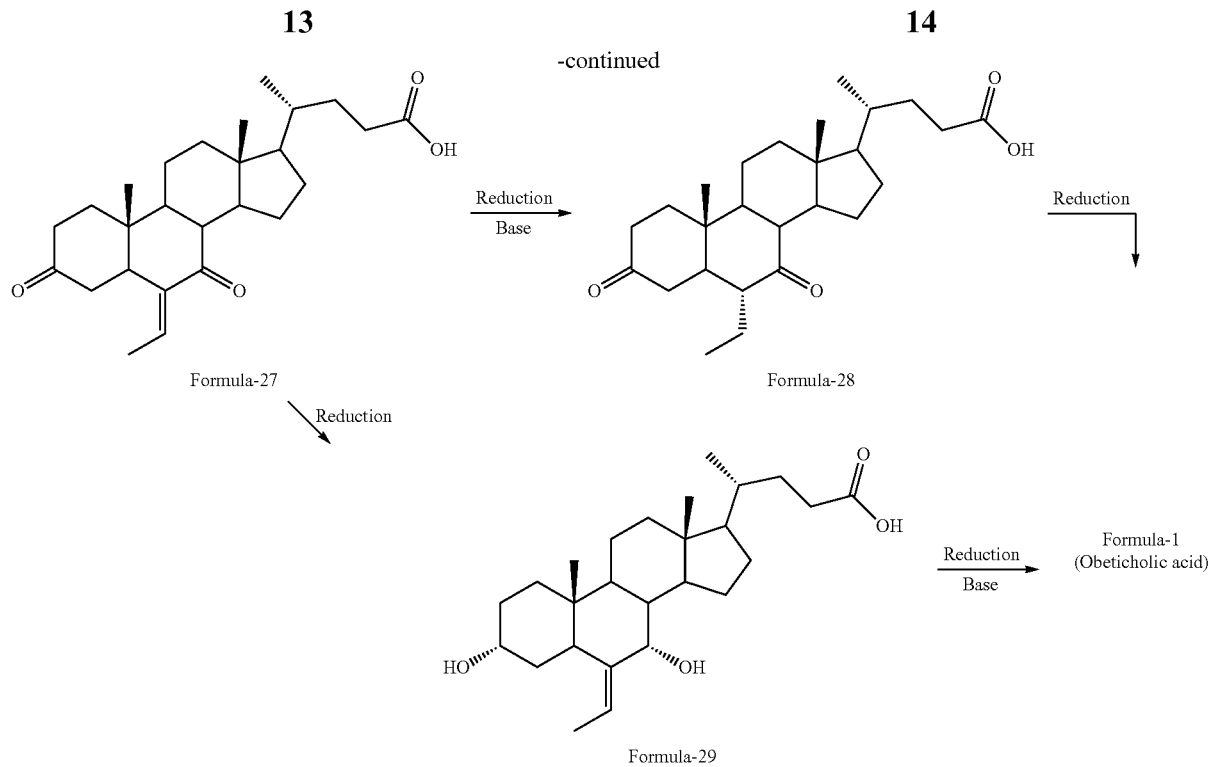
Formula-27
Formula-28
Formula-29
Formula-1 (Obeticholic acid)
R = C1-C6 straight and branched alkyl group
Eighth embodiment of the present invention provides a process for the preparation of Obeticholic acid.
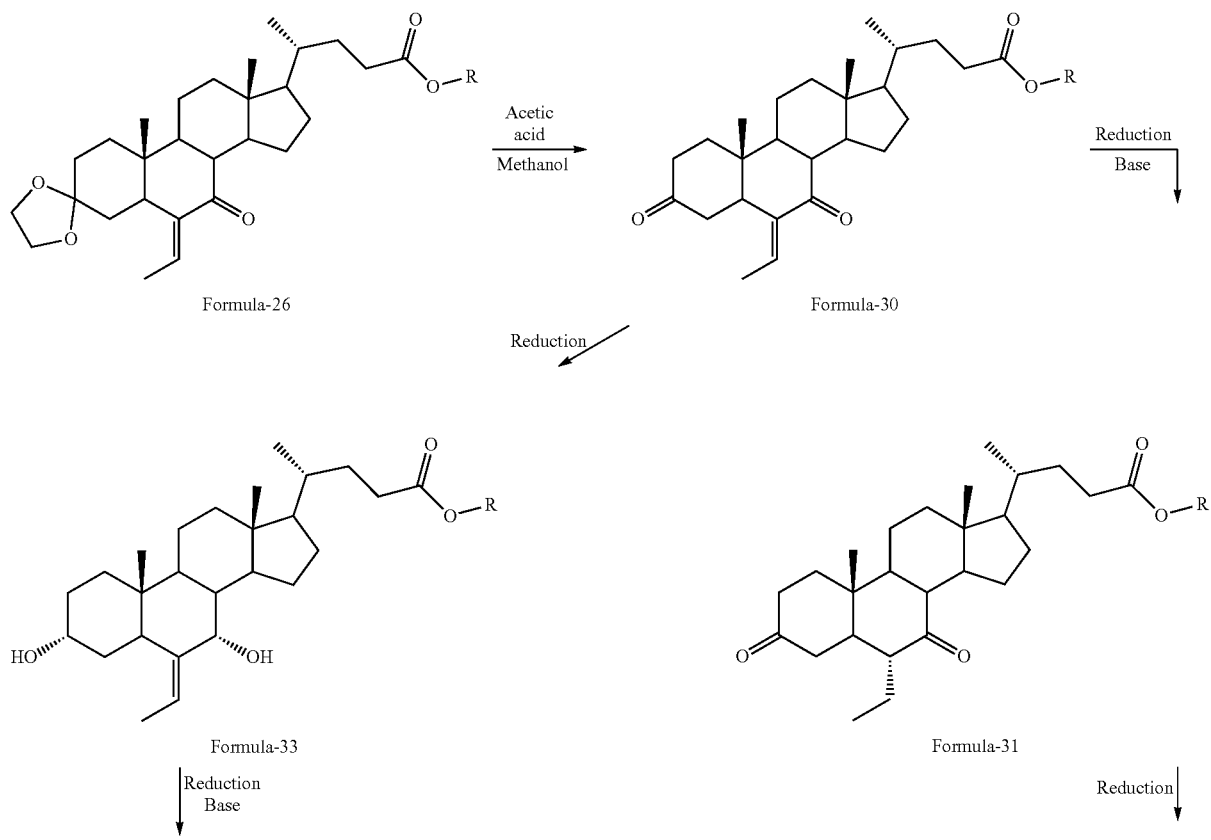
Formula-26
Formula-30
Formula-33
Formula-31

15

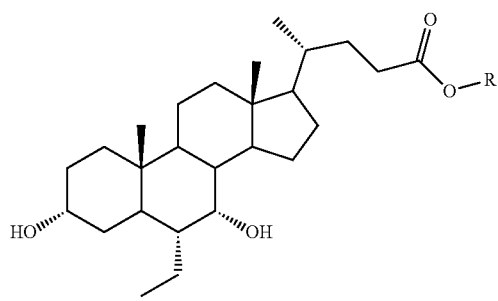

Formula-32

16

-continued

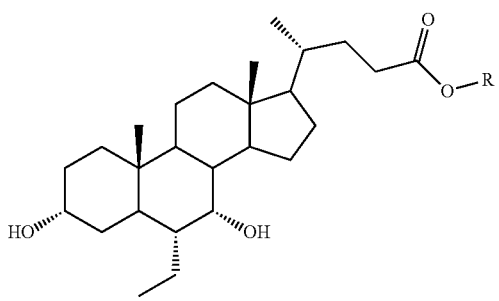

Formula-32

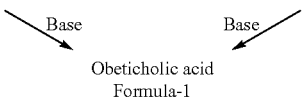

Obeticholic acid
Formula-1

R = C1-C6 straight chain or branched alkyl group

Ninth embodiment of the present invention relates to novel intermediate compounds which are useful in the preparation of Obeticholic acid.

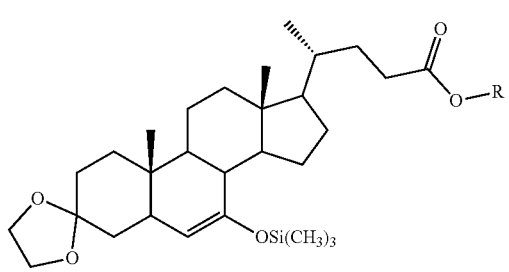

Formula-25

Formula-26

Wherein R is $C_1$-$C_6$ straight chain or branched alkyl group.

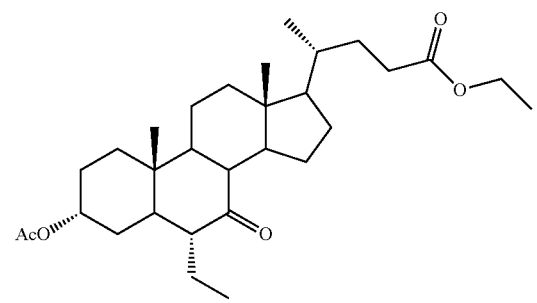

Formula-8

Formula-9

-continued

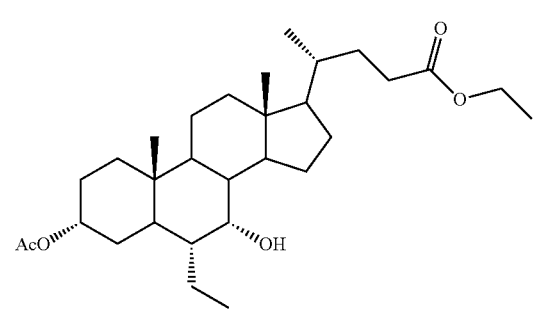

Formula-7

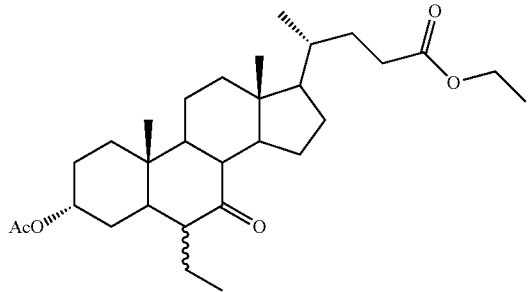

Formula-10

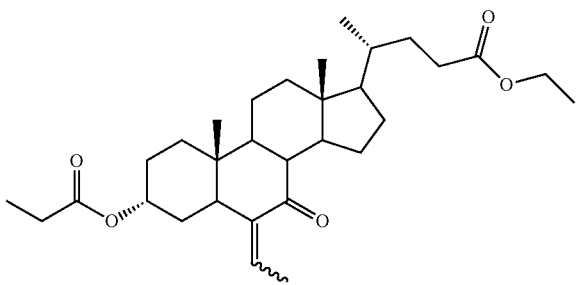

17
-continued

Formula-11
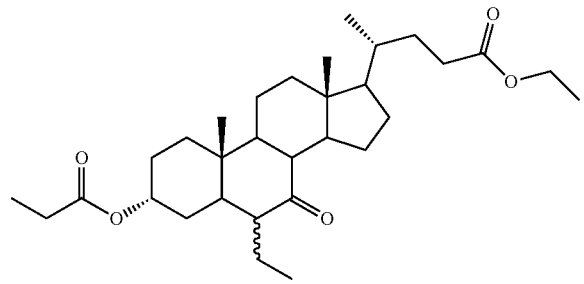

Formula-12
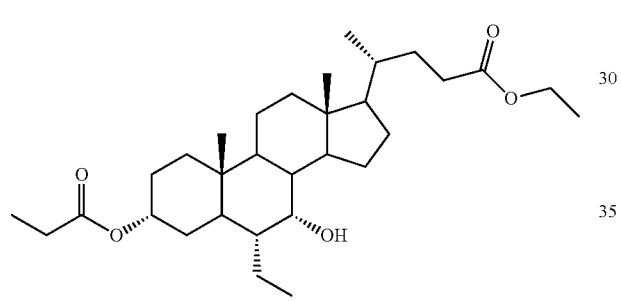

Formula-13
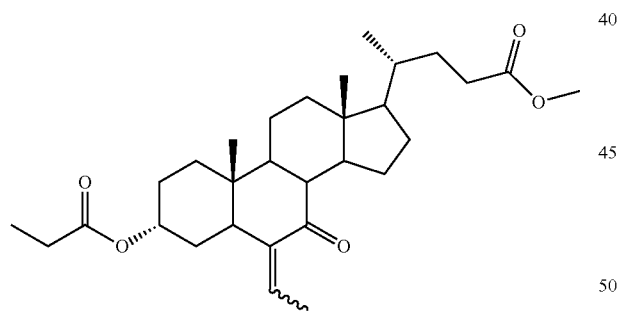

Formula-15
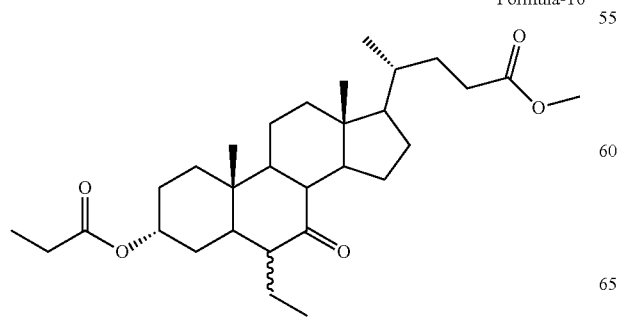

Formula-16
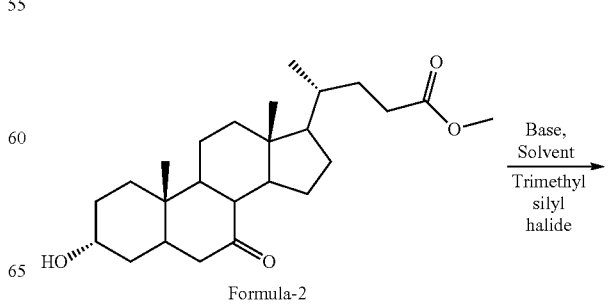

18
-continued

Formula-17
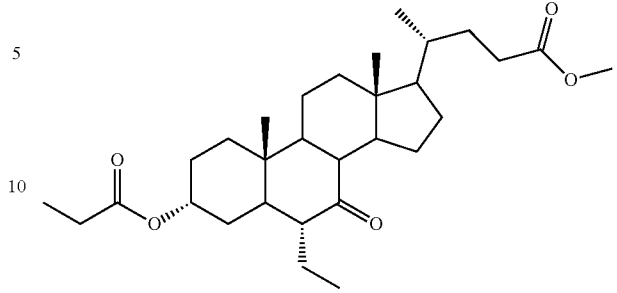

Formula-18
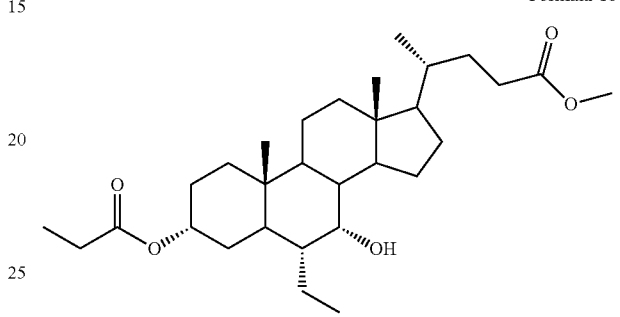

Formula-6
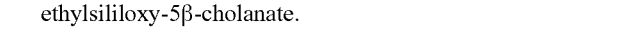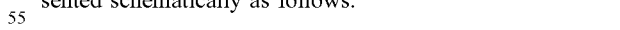

The starting material compound of formula-4 and compound of formula-5 used in the present invention can be prepared from process known in the prior art.

In the tenth embodiment, the present invention provides an improved process for the preparation of methyl 3α,7α-di-trimethylsililoxy-5β-cholanate, comprising reacting methyl 3α-hydroxy-7-keto-5β-cholanate with trimethyl silyl halide in the presence of a suitable base in a suitable solvent at a suitable temperature to provide methyl 3α,7α-di-trimethylsililoxy-5β-cholanate.

In the process of the first embodiment, the preparation of methyl 3α,7α-di-trimethylsililoxy-5β-cholanate is represented schematically as follows:

Formula-2

-continued

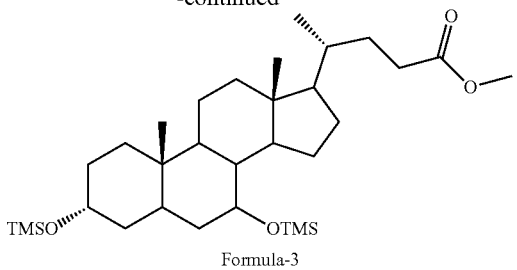

Formula-3

In the process of the first embodiment, trimethyl silyl halide is selected from trimethyl silyl chloride, trimethyl silyl iodide or trimethyl silyl bromide.

In the process of the first embodiment, suitable base is selected from organic or inorganic base.

In the process of the first embodiment, suitable solvent is selected from alcohol solvents, ester solvents, chloro solvents, nitrile solvents, ether solvents, ketone solvents, hydrocarbon solvents, polar aprotic solvents and water or mixture thereof.

In the process of the first embodiment, the reaction is carried out at a temperature of less than 40° C.; preferably of about 0° C. to about 38° C.; more preferably of about 20° C. to about 35° C.

In the eleventh embodiment, the present invention provides crystalline form of Obeticholic acid tertiary butyl amine salt.

In an aspect of the present invention the crystalline form of Obeticholic acid tertiary butyl amine salt is prepared by treating Obeticholic acid with tertiary butyl amine in a suitable solvent.

In the twelfth embodiment, the present invention provides crystalline form-M of Obeticholic acid tertiary butyl amine salt.

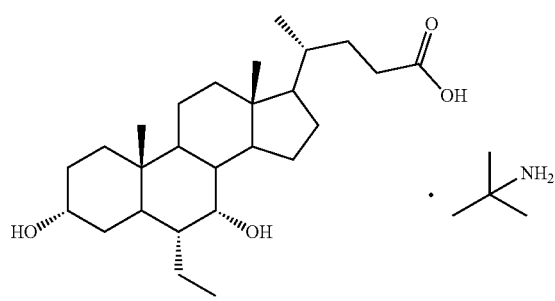

In the twelfth embodiment, the crystalline form-M of Obeticholic acid tertiary butyl amine salt is characterized by its X-ray powder diffraction (XRD) pattern having peaks at about 9.7, 14.6 and 16.8±0.2 degrees 2-theta.

In the twelfth embodiment, the crystalline form-M of Obeticholic acid tertiary butyl amine salt is further characterized by its X-ray powder diffraction (XRD) pattern having peaks at about 8.5, 10.4, 11.5, 11.7, 13.7, 17.2, 17.5, 17.9 and 19.4±0.2 degrees of 2-theta.

Figure 2:
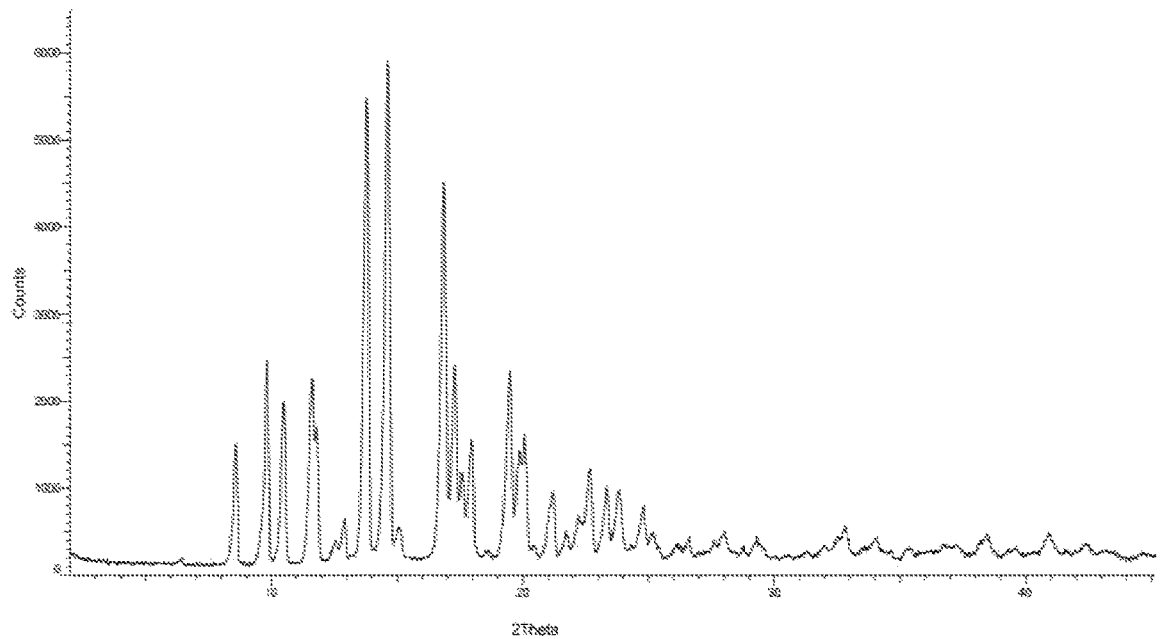
FIG. 2: Illustrates the PXRD pattern of crystalline form-M of Obeticholic acid tertiary butyl amine salt.

In the twelfth embodiment, the crystalline form-M of Obeticholic acid tertiary butyl amine salt is further characterized by its X-ray powder diffraction (XRD) pattern as illustrated in FIG. 2.

In the twelfth embodiment, the crystalline form-M of Obeticholic acid tertiary butyl amine salt is useful in the preparation of pure Obeticholic acid.

In the thirteenth embodiment, the present invention provides a process for the preparation of crystalline form of Obeticholic acid tertiary butyl amine salt, comprising treating Obeticholic acid with tertiary butyl amine in a suitable solvent to provide crystalline form of Obeticholic acid tertiary butyl amine salt.

In the process of the thirteenth embodiment, a suitable solvent used for the preparation of crystalline form of Obeticholic acid tertiary butyl amine salt is selected from alcohol solvents, ester solvents, chloro solvents, nitrile solvents, ether solvents, ketone solvents, hydrocarbon solvents, polar aprotic solvents and water or mixture thereof.

In an aspect of the present invention the crystalline form-M of Obeticholic acid tertiary butyl amine salt can be prepared by treating Obeticholic acid with tertiary butyl amine in a suitable solvent.

Obeticholic acid tertiary butyl amine salt of the present invention can be prepared by using Obeticholic acid prepared according to the present invention or obtained according to any of the prior art known processes or from the process described as per present invention.

In the fourteenth embodiment, the present invention provides a process for the preparation of amorphous Obeticholic acid comprising treating Obeticholic acid tertiary butyl amine salt with a suitable acid in a suitable solvent to provide amorphous Obeticholic acid.

In the process of the fourteenth embodiment, optionally treating the Obeticholic acid tertiary butyl amine salt with a suitable inorganic base in a suitable solvent optionally under nitrogen atmosphere.

Optionally filtering the mixture and treating the resulting filtrate with a suitable acid and isolating provides amorphous Obeticholic acid.

In the process of the fourteenth embodiment, suitable solvent is selected from alcohol solvents, ester solvents, chloro solvents, nitrile solvents, ether solvents, ketone solvents, hydrocarbon solvents, polar aprotic solvents and water or mixture thereof.

In the process of the fourteenth embodiment isolation may be carried out by any methods known in the art. For example employing any of the techniques, but not limited to: decantation, filtration by gravity or suction, centrifugation, adding solvent to make slurry followed by filtration, or other techniques specific to the equipment used and the like, and optionally washing with a solvent.

In the process of the fourteenth embodiment suitable acid is selected from organic or inorganic acid such as hydrochloric acid, sulfuric acid or acetic acid.

In an embodiment, the present invention provides Obeticholic acid having the following "CDCA impurity" less than 0.05%.

In an embodiment, the present invention provides Obeticholic acid having "Isomer-I impurity"; "Dimer impurity"; "3N Acid impurity"; "Isomer-2 impurity' and "Triol impurity" less than 0.03% as measured by HPLC.

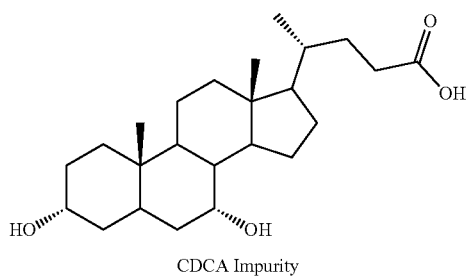

CDCA Impurity

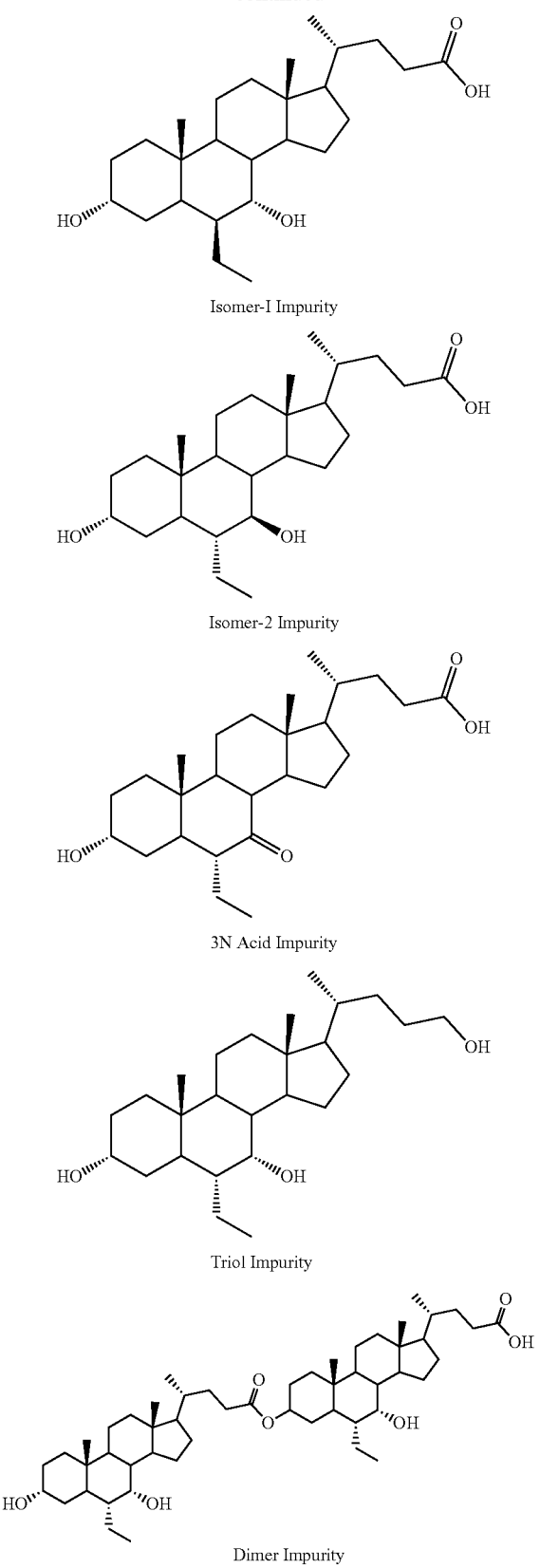

Isomer-1 Impurity

Isomer-2 Impurity

3N Acid Impurity

Triol Impurity

Dimer Impurity

In an embodiment, the present invention provides Obeticholic acid having purity at least about 95%; preferably of at least about 97%; more preferably of at least about 98%; most preferably of at least about 99.9% as measured by HPLC.

In an embodiment, the present invention provides Obeticholic acid having particle size distribution of $D_{90}$ less than 150 μm, preferably less than 100 μm; more preferably 50 μm.

Fifteenth embodiment of the present invention provides a process for the preparation of Obeticholic acid, comprising:

a) Reacting methyl 3α-7α-ditrimethylsilyloxy-5β-chol-6-en-24-oate compound of formula-4 with acetaldehyde in the presence of $BF_3$-etherate in a suitable base in a suitable solvent optionally in the presence of molecular sieves to provide 3α-hydroxy-6-ethylidene-7-keto-5β-cholan-24-oate compound of formula-14 b) reacting compound of formula-14 with a suitable propionylation agent in the presence of a suitable base and in a suitable catalyst in a suitable solvent to provide methyl 3α-propionyloxy-6-ethylidene-7-keto-5β-cholan-24-oate compound of formula-15 c) reducing the compound of formula-15 with a suitable reducing agent in a suitable solvent to provide methyl 3α-propionyloxy-6-ethyl-7-keto-5β-cholan-24-oate compound of formula-16, d) treating the compound of formula-16 with a suitable base in a suitable solvent to provide methyl 3α-propionyloxy-6α-ethyl-7-keto-5β-cholan-24-oate compound of formula-17, e) reducing the compound of formula-17 with a suitable reducing agent in a suitable solvent to provide methyl 3α-propionyloxy-6α-ethyl-7α-hydroxy-5β-cholan-24-oate compound of formula-18, f) treating the compound of formula-18 with a suitable base in a suitable solvent to provide Obeticholic acid compound of formula-1, g) treating the compound of formula-1 with tertiary butyl amine in a suitable solvent to provide Obeticholic acid tertiary butyl amine salt compound of formula-1b, h) optionally purifying the compound of formula-1b with a suitable solvent, i) treating the compound of formula-1b with a suitable acid in a suitable solvent to provide Obeticholic acid compound of formula-1.

In the process of the fifth embodiment, the suitable propionylation agent is selected from propionic anhydride, propionyl chloride; the suitable reducing agent used in step-c) is selected from transition metal catalyst such as copper, nickel, palladium, platinum, rhodium, iridium, and ruthenium in presence of hydrogen gas pressure; the suitable base used in step-a), b), d) and f) is selected from organic or inorganic base; the suitable reducing agent used in step-e) is selected from sodium borohydride, potassium borohydride, sodium cyanoboro hydride, tetramethyl ammonium borohydride, sodium triacetoxy borohydride; the suitable solvent used in step-a) to step-i) is selected from chloro solvents, alcohol solvents, ester solvents, ketone solvents, nitrile solvents, ether solvents, polar aprotic solvents, hydrocarbon solvents and polar solvents like water or mixture thereof.

In the fifteenth embodiment of the present invention process for the preparation of Obeticholic acid is represented schematically as follows:

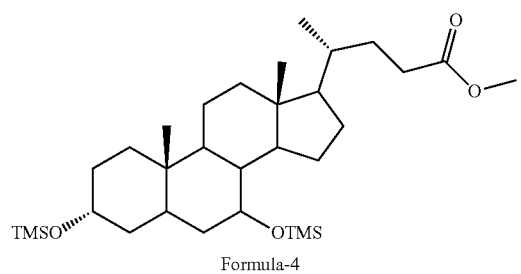

Formula-4

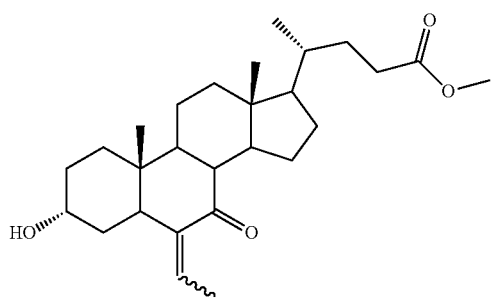

Formula-14

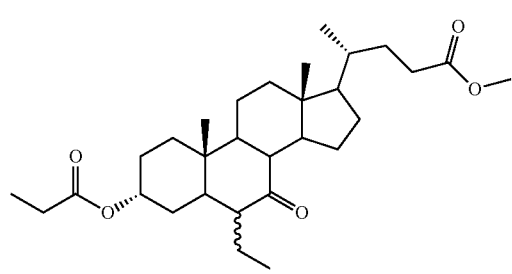

Formula-16

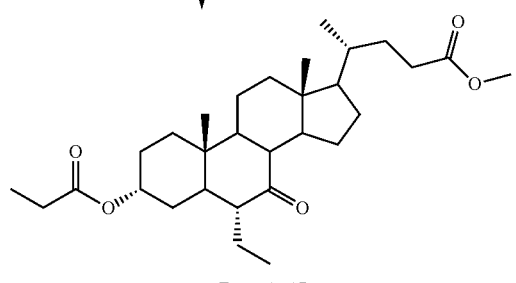

Formula-17

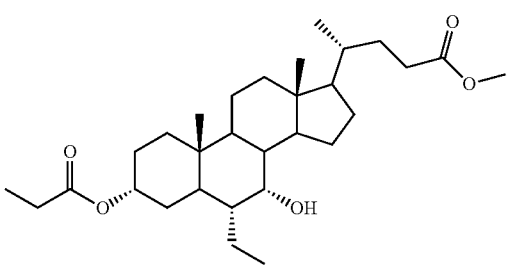

Formula-15

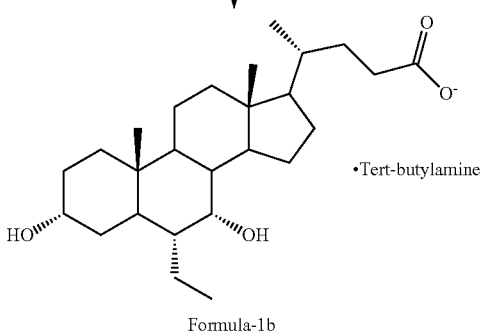

Formula-18

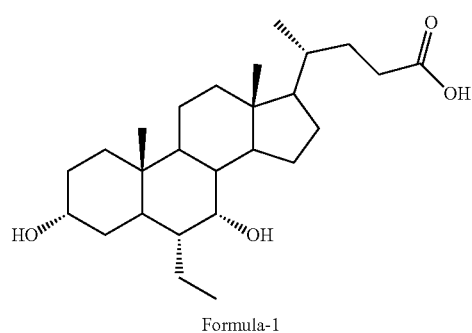

Formula-1
Obeticholic acid

Formula-1b

Obeticholic acid produced by the present invention can be micronized or milled using conventional techniques to get the desired particle size to achieve desired solubility profile to suit to pharmaceutical composition requirements. Techniques that may be used for particle size reduction include, but not limited to ball milling, roller milling and hammer milling. Milling or micronization may be performed before drying, or after the completion of drying of the product.

The invention also encompasses pharmaceutical compositions comprising compound of formula-1 or salts thereof of the present invention. As used herein, the term "pharmaceutical compositions" or "pharmaceutical formulations"

include tablets, pills, powders, liquids, suspensions, emulsions, granules, capsules, suppositories, or injection preparations.

P-XRD Method of Analysis

PXRD analysis of compounds produced by the present invention were carried out using BRUKER D8 ADVANCE/AXS X-Ray diffractometer using Cu Kα radiation of wavelength 1.5406 A° and continuous scan speed of 0.03°/min.

PSD Method of Analysis

Particle size distribution (PSD) analysis was performed using Malvern Mastersizer 2000 instrument.

The process described in the present invention was demonstrated in examples illustrated below. These examples are provided as illustration only and therefore should not be construed as limitation of the scope of the invention

EXAMPLES

Example-1: Preparation of methyl 3α-acetoxy-7α-hydroxy-6α-ethyl-5β-cholanate

Methanol (150 ml) and tetrahydrofuran (150 ml) were added to methyl 3α-acetoxy-7α-keto-6α-ethyl-5β-cholanate (30.0 gms) at 25-30° C. and stirred for 15 minutes at the same temperature. Cooled the reaction mixture to 0-5° C. Sodium borohydride (3.6 gms) was slowly added lot wise to the reaction mixture at 0-5° C. and stirred for 45 minutes at the same temperature. Acetic acid (27 ml) was slowly added to the reaction mixture at 0-5° C. Raised the temperature of reaction mixture to 25-30° C. Distilled off the solvent completely from the reaction mixture under reduced pressure. Ethyl acetate (150 ml) was added to the reaction mixture at 25-30° C. Aqueous sodium bicarbonate solution was added to the reaction mixture at 25-30° C. and stirred for 45 minutes at the same temperature. Both the aqueous and organic layers were separated. Aqueous layer was extracted with ethyl acetate. Combine the organic layer and washed with aqueous sodium carbonate solution. Distilled off the solvent completely from the organic layer under reduced pressure to get the title compound.
Yield: 27.0 gms.

Example-2: Preparation of methyl 3α,7α-dihydroxy-6α-ethyl-5β-cholan-24-oic Acid

Methanol (150 ml) and aqueous sodium hydroxide solution (90 ml) were added to the residue obtained from example-1 at 25-30° C. Heated the reaction mixture to 60-65° C. and stirred for 6 hours at the same temperature. Distilled off the solvent completely from the reaction mixture under reduced pressure. Aqueous sodium bicarbonate solution and ethyl acetate were added to the reaction mixture at 25-30° C. and stirred for 30 minutes at the same temperature. Both the aqueous, organic layers were separated and aqueous layer was extracted twice with ethyl acetate. Ethyl acetate was added to the aqueous layer at 25-30° C. The reaction mixture was acidified using concentrated hydrochloric acid (30 ml) at 25-30° C. and stirred for 30 minutes at the same temperature. Both the aqueous and organic layers were separated. Aqueous layer was extracted with ethyl acetate. Organic layer was combined and washed with water. Active carbon powder was added to the obtained organic layer at 25-30° C. and stirred for 30 minutes at the same temperature. Filtered the reaction mixture through hyflow bed and washed with ethyl acetate. Distilled off the solvent from the obtained filtrate under reduced pressure.

Example-3: Preparation of 3α,7α-dihydroxy-6α-ethyl-5β-cholan-24-oic Acid Ethylene Diamine Salt Ethyl acetate (60 ml) and ethylene diamine (1.51 gms) were added to the compound obtained in example-2 at 25-30° C. Heated the reaction mixture to 60-65° C. and stirred for 45 minutes at the same temperature. Cooled the reaction mixture to 25-30° C. and stirred for 60 minutes at the same temperature. Filtered the precipitated solid and washed with ethyl acetate. N-butyl acetate (150 ml) was added to the obtained wet compound at 25-30° C. Heated the reaction mixture to 85-90° C. and stirred for 45 minutes at the same temperature. Cooled the reaction mixture to 25-30° C. and stirred for 60 minutes at the same temperature. Filtered the solid, washed with n-butyl acetate and dried to get the title compound.
Yield: 22.0 gms. Ethylene diamine content: 10.93%.

Example-4: Preparation of Obeticholic Acid

A mixture of water (1.0 lts) and 3α,7α-dihydroxy-6α-ethyl-5β-cholan-24-oic acid ethylene diamine salt (100 gms) was stirred for 30 minutes at 25-30° C. Filtered the reaction mixture through 0.2μ filter paper and washed with water. The obtained filtrate was added to aqueous hydrochloric acid solution (41.6 ml) at 25-30° C. and stirred for 60 minutes at the same temperature. Filtered the solid and washed with water. To the obtained wet compound, water (200 ml) was added at 25-30° C. and stirred for 60 minutes at the same temperature. Filtered the solid and washed with water. Water (200 ml) was added to the obtained wet compound at 25-30° C. and stirred for 60 minutes at the same temperature. Filtered the solid, washed with water and dried to get the title compound. Yield: 70.0 gms.

Example-5: Preparation of methyl 3α-hydroxy-7-keto-5β-cholanate

Concentrated sulfuric acid (1.0 ml) was slowly added to a mixture of methanol (250 ml) and 3α-hydroxy-7-keto-5β-cholanic acid (50 gms) at 25-30° C. Heated the reaction mixture to 50-55° C. and stirred for 3 hours at the same temperature. Cooled the reaction mixture to 25-30° C. Aqueous sodium bicarbonate solution was slowly added to the reaction mixture at 25-30° C. and stirred for 60 minutes at the same temperature. Filtered the solid and washed with water. Ethyl acetate (75 ml) was added to the obtained wet compound at 25-30° C. Heated the reaction mixture to 45-50° C. and stirred for 50 minutes at the same temperature. Reaction mixture was washed with aqueous sodium chloride solution. Both the aqueous and organic layers were separated. N-heptane was slowly added to the obtained organic layer within 2 hours at 25-30° C. and stirred for 60 minutes at the same temperature. Filtered the precipitated solid, washed with a mixture of ethyl acetate, heptane and dried to get the title compound. Yield: 43.0 gms; Reported M.R: 62-64° C.

Example-6: Preparation of methyl 3α-7α-ditrimethylsilyloxy-5β-chol-6-en-24-oate

A mixture of methyl 3α-hydroxy-7-keto-5β-cholanate (100 gms) and toluene (1.0 lts) were stirred for 10 minutes at 25-30° C. Heated the reaction mixture to 110-115° C. for 2 hours and traces amount of water was removed azeotropically through dean-stark apparatus from the reaction mixture. Distilled off the half of the solvent from the reaction mixture under reduced pressure. A mixture of sodium iodide (166.7 gms), toluene (1.0 lts) and acetonitrile (500 ml) was heated to 110-115° C. for 2 hours and traces amount of water was removed azeotropically through dean-stark apparatus from the reaction mixture. Distilled off the half of the solvent from the reaction mixture under reduced pressure. Cooled the reaction mixture to 25-30° C. Triethyl amine (137.5 gms) and acetonitrile (500 ml) were added to the reaction mixture. The above obtained methyl ester solution was added to the reaction mixture under inert atmosphere at 25-30° C. Chlorotrimethyl silane (120.8 gms) was slowly added to the reaction mixture. Heated the reaction mixture to 50-55° C. and stirred for 3 hours at the same temperature. Cooled the reaction mixture to 10-15° C. Aqueous sodium thiosulphate pent hydrate solution was added to the reaction mixture at 10-15° C. and stirred for 10 minutes at the same temperature. Raised the temperature of the reaction mixture to 25-30° C. Both the aqueous and organic layers were separated and aqueous layer was extracted with toluene. Combined the organic layers and washed with aqueous sodium bicarbonate solution. Distilled off the solvent completely from the organic layer under reduced pressure.

Example-7: Preparation of 3α-hydroxy-6-ethylidene-7-keto-5β-cholan-24-oic Acid

Triethyl amine, sulfuric acid (1.0 ml) and dichloromethane (500 ml) were added to a pre-cooled paraldehyde (65.3 gms) at 10-15° C. The compound obtained in example-6 and dichloromethane were added to the reaction mixture at 10-15° C. Molecular sieves (100 gms) were added to the reaction mixture and cooled the reaction mixture to −75 to −80° C. Boron trifluoride diethyl etherate (157.8 gms) was slowly added to the reaction mixture at −75 to −80° C. and stirred for 2 hours at the same temperature. Raised the temperature of the reaction mixture to 25-30° C. and stirred for 1 hour at the same temperature. Filtered the reaction mixture and washed with dichloromethane. Water was added to the obtained filtrate at 25-30° C. and stirred for 30 minutes at the same temperature. Both the aqueous and organic layers were separated and organic layer was washed twice with aqueous sodium bicarbonate solution. Distilled off the solvent completely from the organic layer under reduced pressure followed by co-distilled with ethyl acetate. Aqueous sodium hydroxide solution was added to a mixture of above obtained residue and methanol at 25-30° C. Heated the reaction mixture to 60-65° C. and stirred for 3 hours at the same temperature. Distilled-off the solvent from the reaction mixture under reduced pressure. Aqueous hydrochloric acid solution was slowly added to the reaction mixture at 25-30° C. and stirred for 1 hour at the same temperature. Filtered the precipitated solid and washed with water. Cyclohexane was added to the obtained solid at 25-30° C. and stirred for 30 minutes at the same temperature. Filtered the solid and washed with cyclohexane. Acetone was added to the obtained wet solid at 25-30° C. Heated the reaction mixture to 50-55° C. and stirred for 45 minutes at the same temperature. Cooled the reaction mixture to 0-5° C. and stirred for 1 hour at the same temperature. Filtered the solid, washed with acetone and dried to get title compound.
Yield: 35.0 gms.

Example-8: Purification of 3α-hydroxy-6-ethylidene-7-keto-5β-cholan-24-oic Acid

Acetone was added to 3α-hydroxy-6-ethylidene-7-keto-5β-cholan-24-oic acid obtained in example-7 at 25-30° C. and stirred for 10 minutes at the same temperature. Heated the reaction mixture to 50-55° C. and stirred for 45 minutes at the same temperature. Cooled the reaction mixture to 0-5° C. and stirred for 60 minutes at the same temperature. Filtered the precipitated solid, washed with pre-cooled acetone and died to get the title compound.
Yield: 35.0 gms.

Example-9: Preparation of methyl 3α-hydroxy-6-ethylidene-7-keto-5β-cholan-24-oate: Formula-14

Concentrated sulfuric acid (2.0 ml) was added to a mixture of 3α-hydroxy-6-ethylidene-7-keto-5β-cholan-24-oic acid (100 gms) and methanol (500 ml) at 25-30° C. Heated the reaction mixture to 50-55° C. and stirred for 3 hours at the same temperature. Cooled the reaction mixture to 25-30° C. and aqueous sodium bicarbonate solution was added to the reaction mixture at the same temperature. Ethyl acetate (300 ml) was added to the reaction mixture at 25-30° C. and stirred for 20 minutes at the same temperature. Both the aqueous and organic layers were separated and aqueous layer was extracted with ethyl acetate.

Example-10: Preparation of methyl 3α-propionyloxy-6-ethylidene-7-keto-5β-cholan-24-oate: Formula-15

Triethyl amine (48.61) and dimethylamino pyridine (1.4 gms) were added to the obtained organic layer in example-9 at 25-30° C. Cooled the reaction mixture to 0-5° C. Propionic anhydride (46.89 gms) was slowly added to the reaction mixture at 0-5° C. and stirred for 15 minutes at the same temperature. Raised the temperature of the reaction mixture to 25-30° C. and stirred for 3 hours at the same temperature. Cooled the reaction mixture to 10-15° C. Aqueous sodium bicarbonate solution was added to the reaction mixture at 10-15° C. and stirred for 30 minutes at the same temperature. Both the aqueous and organic layers were separated. Aqueous layer was extracted with ethyl acetate. Combined the organic layers and washed with aqueous citric acid solution followed by sodium bicarbonate solution.

Example-11: Preparation of methyl 3α-propionyloxy-6-ethyl-7-keto-5β-cholan-24-oate: Formula-16

Pd/C (30 gms) and the organic layer obtained in example-10 were added into an autoclave under inert atmosphere and autoclave was pressurized with 5 kg/cm$^2$ of hydrogen gas. Heated the reaction mixture to 50-55° C. and stirred for 10 hours at the same temperature. Cooled the reaction mixture to 25-30° C. and filtered through hyflow bed and washed with ethyl acetate. Distilled off the solvent completely from the obtained filtrate under reduced pressure and co-distilled with toluene to get the title compound.

Example-12: Preparation of methyl 3α-propionyloxy-6α-ethyl-7-keto-5β-cholan-24-oate: Formula-17

Toluene (200 ml) was added to the obtained compound in example-11 at 25-30° C. Heated the reaction mixture to 110-115° C. and stirred for 2 hours to remove the traces amount of water azeotropically through dean-stak apparatus from the reaction mixture. Cooled the reaction mixture to 50-55° C. 1,8-Diazabicyclo[5.4.0] undec-7-ene (123.7 gms) was added to the reaction mixture at 65-70° C. Heated the reaction mixture to 110-115° C. and stirred for 22 hours at the same temperature. Cooled the reaction mixture to 25-30° C. and washed with aqueous sodium chloride solution. Both the aqueous and organic layers were separated. Aqueous layer was extracted with toluene. Combined the organic layers and washed with sodium bicarbonate solution followed by water. Distilled off the solvent completely from the organic layer under reduced pressure and co-distilled with methanol. Methanol (200 ml) was added to the obtained residue at 25-30° C. Heated the reaction mixture to 60-65° C. and stirred for 30 minutes at the same temperature. Cooled the reaction mixture to 0-5° C. and stirred for 2 hours at the same temperature. Filtered the precipitated solid, washed with pre-cooled methanol and dried to get the title compound. Yield: 30 gms.

Example-13: Preparation of methyl 3α-propionyloxy-6α-ethyl-7α-hydroxy-5β-cholan-24-oate: Formula-18

Methanol (150 ml) and tetrahydrofuran (150 ml) were added to methyl 3α-propionyloxy-6α-ethyl-7-keto-5β-cholan-24-oate (30 gms) at 25-30° C. and stirred for 15 minutes at the same temperature. Cooled the reaction mixture to 0-5° C. Sodium borohydride (3.6 gms) was slowly added lot wise to the reaction mixture at 0-5° C. and stirred for 45 minutes at the same temperature. Acetic acid (27 ml) was slowly added to the reaction mixture at 0-5° C. Raised the temperature of reaction mixture to 25-30° C. Distilled off the solvent completely from the reaction mixture under educed pressure. Ethyl acetate (150 ml) was added to the reaction mixture at 25-30° C. Aqueous sodium bicarbonate solution was added to the reaction mixture at 25-30° C. and stirred for 45 minutes at the same temperature. Both the aqueous and organic layers were separated. Aqueous layer was extracted with ethyl acetate. Combine the organic layer and washed with aqueous sodium carbonate solution. Distilled off the solvent completely from the organic layer under reduced pressure.

Example-14: Preparation of 3α,7α-dihydroxy-6α-ethyl-5β-cholan-24-oic Acid Ethylene Diamine Salt: Formula-1a Methanol (150 ml) and aqueous sodium hydroxide solution (90 ml) were added to the compound obtained from example-13 at 25-30° C. Heated the reaction mixture to 60-65° C. and stirred for 6 hours at the same temperature. Distilled off the solvent completely from the reaction mixture under reduced pressure. Toluene and water were added to the obtained residue at 25-30° C. and stirred for 30 minutes at the same temperature. Both the aqueous and organic layers were separated. Aqueous layer was extracted with toluene. The aqueous layer was acidified using concentrated hydrochloric acid (30 ml) at 25-30° C. and stirred for 30 minutes at the same temperature. Both the aqueous and organic layers were separated. Aqueous layer was extracted with ethyl acetate. Organic layer was combined and washed with water. Active carbon powder was added to the obtained organic layer at 25-30° C. and stirred for 30 minutes at the same temperature. Filtered the reaction mixture through hyflow bed and washed with ethyl acetate. Distilled off the solvent from the obtained filtrate under reduced pressure. Ethyl acetate (60 ml) and ethylene diamine (1.47 gms) were added to the reaction mixture at 25-30° C. Heated the reaction mixture to 60-65° C. and stirred for 45 minutes at the same temperature. Cooled the reaction mixture to 25-30° C. and stirred for 60 minutes at the same temperature. Filtered the precipitated solid and washed with ethyl acetate. Ethyl acetate (150 ml) was added to the obtained wet compound at 25-30° C. Heated the reaction mixture to 65-70° C. and stirred for 45 minutes at the same temperature. Cooled the reaction mixture to 25-30° C. and stirred for 1 hour at the same temperature. Filtered the precipitated solid, washed with ethyl acetate and dried to get the title compound.
Yield: 22.0 gms; The PXRD pattern of the obtained compound was depicted in FIG. 1.

Example-15: Preparation of ethyl 3α-propionyloxy-6-ethylidene-7-keto-5β-cholan-24-oate: Formula-10

Ethyl acetate (135 ml) was added to compound of formula-5 (27.0 gms) at 25-30° C. and stirred for 20 minutes at the same temperature. Triethyl amine (16.9 ml) and DMAP (0.37 gms) were added to the reaction mixture at 25-30° C. and stirred for 10 minutes at the same temperature. Cooled the reaction mixture to 0-5° C. Propionic anhydride (11.86 gms) was slowly added to the reaction mixture at 0-5° C. and stirred for 20 minutes at the same temperature. Raised the temperature of reaction mixture to 25-30° C. Cooled the reaction mixture to 0-5° C. 5% Sodium bicarbonate was slowly added to the reaction mixture at 0-5° C. Raised the temperature of reaction mixture to 25-30° C. Both the organic layer and aqueous layers were separated and extracted the aqueous layer using ethyl acetate. Combined the total organic layers and washed with sodium chloride solution. Distilled off the solvent completely from the organic layer under reduced pressure to get the title compound. Yield: 29.0 gms.

Example-16: Preparation of ethyl 3α-propionyloxy-6-ethyl-7-keto-5β-cholan-24-oate: Formula-11

A mixture of compound of formula-10 (280 gms), ethyl acetate (224 ml) and palladium carbon (8.4 gms) were charged into an autoclave vessel. Hydrogen gas with a pressure of 5.0 Kg/cm$^2$ was applied to the above mixture at 25-30° C. Raised the temperature of reaction mixture to 60-65° C. and stirred for 8 hours at the same temperature. Cooled the reaction mixture to 25-30° C. Filtered through hyflo bed and washed with ethyl acetate. Distilled off the solvent completely from the filtrate under reduced pressure to get the title compound. Yield: 27.0 gms.

Example-17: Preparation of ethyl 3α-propionyloxy-6α-ethyl-7-keto-5β-cholan-24-oate: Formula-12.

Toluene (260 ml) was added to compound of formula-11 (26.0 gms) at 25-30° C. The reaction mixture was slowly heated to reflux through azotropic distillation mode and stirred for 2 hours at azeotropic reflux. After completion of the reaction, the reaction mixture was cooled to 25-30° C. 1,8-diazabicyclo[5.4.0]undec-7-ene (47.55 gms) was slowly added to the reaction mixture at 25-30° C. and stirred for 1 hour at the same temperature. Raised the temperature of reaction mixture to 110° C. and stirred for 5 hours at same temperature. Cooled the reaction mixture to 25-30° C. Sodium chloride solution was added to the reaction mixture at 25-30° C. and stirred for 30 minutes at the same temperature. Both the organic layer and aqueous layers were separated and extracted the aqueous layer using toluene. Combined the total organic layers and washed with water. Distilled off the solvent completely from the organic layer under reduced pressure to get the title compound. Yield: 21.0 gms.

The compound of formula-12 of the present invention can be converted into Obeticholic acid.

Example-18: Preparation of ethyl 3α-methoxymethoxy-6-ethylidene-7-keto-5β-cholan-24-oate: Formula-19

Methylene chloride (35 ml) was added to compound of formula-5 (7.0 gms) at 25-30° C. and stirred for 20 minutes at the same temperature. Diisopropylethyl amine (10 gms) was slowly added to the reaction mixture at 25-30° C. and stirred for 10 minutes at the same temperature. Cooled the reaction mixture to 0-5° C. Methoxymethyl chloride (6.3 gms) was slowly added to the reaction mixture at 0-5° C. and stirred for 30 minutes at the same temperature. Raised the temperature of reaction mixture to 25-30° C. Diisopropylethyl amine was added to the reaction mixture at 25-30° C. and stirred for 3 hours at the same temperature. Water was slowly added to the reaction mixture at 25-30° C. and stirred for 10 minutes at the same temperature. Ethyl acetate was added to the reaction mixture at 25-30° C. and stirred for 20 minutes at the same temperature. Both the organic layer and aqueous layers were separated and extracted the aqueous layer using ethyl acetate. Combined the total organic layers and washed with sodium chloride solution. Distilled off the solvent completely from the organic layer under reduced pressure to get the title compound. Yield: 6.5 gms.

Example-19: Preparation of Compound of Formula-20

A mixture of compound of formula-19 (6.4 gms), ethyl acetate (150 ml) and palladium carbon (3.5 gms) were charged into an autoclave vessel. Raised the temperature of the reaction mixture to 60-65° C. and stirred for 20 minutes at the same temperature. Hydrogen gas with a pressure of 5.0 Kg/cm² was applied to the above mixture at 60-65° C. Cooled the reaction mixture to 25-30° C. Filtered through hyflo bed and washed with ethyl acetate. Distilled off the solvent completely from the filtrate under reduced pressure to get the title compound. Yield: 5.2 gms.

Example-20: Preparation of Compound of Formula-21

Toluene (50 ml) was added to compound of formula-20 (5.0 gms) at 25-30° C. and stirred for 30 minutes at the same temperature. Heated the reaction mixture to reflux temperature and stirred for 3 hours at the same temperature. Cooled the reaction mixture to 60-65° C. 1,8-diazabicyclo[5.4.0]undec-7-ene (5.43 gms) was added to the reaction mixture at 60-65° C. and stirred for 25 minutes at the same temperature. Heated the reaction mixture to reflux temperature and stirred for 4 hours at the same temperature. DBU was added to the reaction mixture at reflux temperature and stirred for 5 hours at the same temperature. Cooled the reaction mixture to 25-30° C. Sodium chloride solution was added to the reaction mixture at 25-30° C. and stirred for 30 minutes at the same temperature. Both the organic layer and aqueous layers were separated and extracted the aqueous layer using toluene. Combined the total organic layers and washed with water. Distilled off the solvent completely from the organic layer under reduced pressure to get the title compound. Yield: 4.5 gms.

The compound of formula-21 of the present invention can be converted into Obeticholic acid.

Example-21: Preparation of Compound of Formula-24

Toluene (20 ml) was added to compound of formula-23 (1.0) at 25-30° C. and stirred for 25 minutes at the same temperature. p-toluene sulfonic acid (mg) and ethylene glycol (0.012 gms) were added to the reaction mixture at 25-30° C. and stirred for 15 minutes at the same temperature. Heated the reaction mixture to 50-60° C. and stirred for 5 hours at the same temperature. Cooled the reaction mixture to 25-30° C. Water and ethyl acetate was added to the reaction mixture at 25-30° C. and stirred for 30 minutes at the same temperature. Both the organic layer and aqueous layers were separated and extracted the aqueous layer using ethyl acetate. Combined the total organic layers and washed with sodium chloride solution. Distilled off the solvent completely from the organic layer under reduced pressure to get the title compound. Yield: 0.7 gms.

Example-22: Preparation of Compound of Formula-25

Toluene (10 ml) was added to compound of formula-24 (1.0) at 25-30° C. The reaction mixture was heated to reflux through azotropic distillation mode and stirred for 2 hours at azeotropic reflux. Cooled the reaction mixture to 25-30° C. Acetonitrile (10 ml) and NaI (1.5 gms) was added to the reaction mixture at 25-30° C. and stirred for 15 minutes at the same temperature. Raised the temperature of the reaction mixture to 60-70° C. Toluene was added to the reaction mixture at 60-70° C. and stirred for 20 minutes at the same temperature. Heated the reaction mixture to reflux temperature and stirred for 2 hours at the same temperature. Cooled the reaction mixture to 25-30° C. Triethyl amine (1.7 ml) was added to the reaction mixture at 25-30° C. and stirred for 30 minutes at the same temperature. Trimethyl silyl chloride (1.28 ml) was added to the reaction mixture at 25-30° C. and stirred for 20 minutes at the same temperature. Heated the reaction mixture to 50-60° C. and stirred for 4 hours at the same temperature. Cooled the reaction mixture to 25-30° C. and stirred for 15 minutes at the same temperature. Sodium bicarbonate solution was added to the reaction mixture at 25-30° C. and stirred for 15 minutes at the same temperature. Both the organic layer and aqueous layers were separated and extracted the aqueous layer using ethyl acetate. Combined the total organic layers and washed with sodium chloride solution. Distilled off the solvent completely from the organic layer under reduced pressure to get the title compound. Yield: 1.0 gms.

Example-23: Preparation of Compound of Formula-26

Methylene chloride (15 ml) was added to compound of formula-25 (1.0 gms) at 25-30° C. and stirred for 10 minutes at the same temperature. Cooled the reaction mixture to −78° C. to −75° C. Acetaldehyde (0.42 ml) and Boron trifluoride etherate (1.4 ml) were added to the reaction mixture at −78° C. to −75° C. and stirred for 2 hours at the same temperature. Raised the temperature of the reaction mixture to 25-30° C. and stirred for 2 hours at the same temperature. Filtered through hyflo bed and washed with methylene chloride. The obtained filtrate washed with sodium bicarbonate solution at 25-30° C. and stirred for 15 minutes at the same temperature. Both the organic layer and aqueous layers were separated and organic layer washed with sodium chloride solution. Distilled off the solvent completely from the organic layer under reduced pressure to get the title compound. Yield: 0.6 gms.

The compound of formula-26 of the present invention can be converted into Obeticholic acid.

Example-24: Preparation of methyl 3α-hydroxy-7-keto-5β-cholanate

Concentrated sulfuric acid (1.0 ml) was slowly added to a mixture of 3α-hydroxy-7-keto-5β-cholic acid (50 gms) and methanol (250 ml) at 25-30° C. and stirred for 15 minutes at the same temperature. Heated the reaction mixture to 50-55° C. and stirred for 3 hours at the same temperature. Cooled the reaction mixture to 10-15° C. Slowly added aqueous sodium bicarbonate solution to the reaction mixture at 10-15° C. Raised the temperature of the reaction mixture to 25-30° C. and stirred for 1 hour at the same temperature. Filtered the precipitated solid and washed with water. To the obtained compound, water (100 ml) at 25-30° C. and stirred for 1 hour at the same temperature. Filtered the solid, washed with water and dried to get the title compound. Yield: 43.0 gms; M.R: 85-90° C. Purity by HPLC: 99.4%.

Example-25: Preparation of methyl 3α,7α-di-trimethylsililoxy-5β-cholanate

Aqueous sodium bicarbonate solution was added to toluene (500 ml) and methyl 3α-hydroxy-7-keto-5β-cholanate (100 gms) at 25-30° C. Layers were separated. Organic layer was heated to 100-110° C. and stirred for 2 hours at the same temperature. Distilled off the solvent from the reaction mixture under reduced pressure. Toluene (500 ml) was added to the obtained compound at 25-30° C. under nitrogen atmosphere to get mixture 1. A mixture of toluene (500 ml), acetonitrile (300 ml) and sodium iodide (166.74 gms) were stirred at 25-30° C. under nitrogen atmosphere. Heated the mixture to 90-95° C. and stirred for 2 hours at the same temperature. Distilled off the solvent from the mixture under reduced pressure. Acetonitrile (500 ml) and triethyl amine (137.5 gms) were added to the obtained compound at 25-30° C. under nitrogen atmosphere to get mixture 2. The above mixture 1 is added to the mixture 2 at 25-30° C. under nitrogen atmosphere. Chlorotrimethyl silane (120.84 gms) was added to the reaction mixture at 25-30° C. and stirred for 8 hours at the same temperature. Cooled the mixture to 5-10° C. Aqueous sodium bicarbonate solution and sodium thiosulphate pentahydrate was added to the reaction mixture at 5-10° C. Raised the temperature of the reaction mixture 25-30° C. Layers were separated and extracted the aqueous layer with toluene. Combined the organic layers and aqueous sodium bicarbonate solution was added to it at 25-30° C. Layers were separated. Distilled off the solvent from the organic layer completely under reduced pressure to get the title compound. Yield: 140 gms.

Example-26: Preparation of methyl 3α-hydroxy-6-ethyliden-7-keto-5β-cholanate Dichloromethane (200 ml) was added to the compound obtained in example-25 at 25-30° C. Molecular sieves (100 gms) were added to the reaction mixture at 25-30° C. under nitrogen atmosphere. Cooled the reaction mixture to −70 to −75° C. Acetaldehyde (43.5 gms), triethyl amine (50.02 gms), BF$_3$-etherate (157.87 gms) and dichloromethane (200 ml) was added to the reaction mixture at −70 to −75° C. and stirred for 3 hours at the same temperature. Raised the temperature of the mixture to 25-30° C. and stirred for 2 hours at the same temperature. Filtered the reaction mixture and washed with dichloromethane. The obtained filtrate was added to aqueous sodium bicarbonate solution at 25-30° C. Layers were separated. Aqueous sodium bicarbonate solution was added to the organic layer at 25-30° C. Layers were separated. Combined the organic layers and distilled off the solvent completed under reduced pressure. N-heptane (200 ml) was added to obtained compound at 25-30° C. and stirred for 15 minutes at the same temperature. Filtered the precipitated solid to get the title compound.
Yield: 94.0 gms.

Example-27: Preparation of methyl 3α-hydroxy-6-ethyliden-7-keto-5β-cholanate Dichloromethane (100 ml) was added to the compound obtained in example-25 at 25-30° C. Molecular sieves (50 gms) were added to the reaction mixture at 25-30° C. under nitrogen atmosphere. Cooled the reaction mixture to −70 to −75° C. Acetaldehyde (21.75 gms), triethyl amine (25.0 gms), BF$_3$-etherate (96.47 gms) and dichloromethane (100 ml) was added to the reaction mixture at −70 to −75° C. and stirred for 3 hours at the same temperature. Raised the temperature of the mixture to 25-30° C. and stirred for 2 hours at the same temperature. Filtered the reaction mixture and washed with dichloromethane. The obtained filtrate was slowly added to aqueous sodium bicarbonate solution at 25-30° C. Layers were separated. Aqueous sodium bicarbonate solution was added to the organic layer at 25-30° C. Layers were separated. Combined the organic layers and distilled off the solvent completed under reduced pressure. N-heptane (100 ml) was added to obtained compound at 25-30° C. and stirred for 15 minutes at the same temperature. Filter the compound. Ethyl acetate was added to obtained compound at 25-30° C. and stirred for 15 minutes at the same temperature. Distilled off the solvent completely under reduced pressure to get the title compound. Yield: 43.0 gms.

Example-28: Preparation of methyl 3α-propionyloxy-6-ethylidene-7-keto-5β-cholan-24-oate A mixture of ethyl acetate (500 ml), triethylamine (47.0 gms), dimethylamino pyridine (1.4 gms) and methyl 3α-hydroxy-6-ethyliden-7-keto-5β-cholanate (100 gms) were cooled to 0-5° C. Propionic anhydride (45.3 gms) was slowly added to the reaction mixture at 0-5° C. Raised the temperature of the mixture to 25-30° C. and stirred for 3 hours at the same temperature. Cooled the mixture to 10-15° C. Aqueous sodium bicarbonate solution was added to the mixture at 10-15° C. Layers were separated and aqueous layer was extracted with ethyl acetate. Combined the organic layers and washed with aqueous citric acid solution followed by sodium bicarbonate solution. Active carbon (5.0 gms) and sodium sulphate was added to the organic layer at 25-30° C. and stirred for 30 minutes at the same temperature. Filtered the reaction mixture through hyflow bed and washed the bed with ethyl acetate to get the title compound.

Example-29: Preparation of methyl 3α-propionyloxy-6-ethyl-7-keto-5β-cholan-24-oate A mixture of palladium hydroxide (15.0 gms) and ethyl acetate (100 ml) was added to the compound obtained in example-28 at 25-30° C. under nitrogen atmosphere. Autoclave was pressurized with 5 kg/cm² of hydrogen gas. Heated the mixture to 50-55° C. and stirred for 8 hours at the same temperature. Cooled the mixture to 25-30° C. and filtered through hyflow bed and washed with ethyl acetate. Distilled off the solvent completely from the obtained filtrate under reduced pressure to get the title compound. Yield: 95.0 gms.

Example-30: Preparation of methyl 3α-propionyloxy-6α-ethyl-7-keto-5β-cholan-24-oate Toluene (600 ml) was added to the compound obtained in example-29 at 25-30° C. Heated the mixture to 110-115° C. and stirred for 2 hours to remove the traces amount of water azeotropically from the mixture. Cooled the mixture to 50-55° C. 1,8-diazabicyclo[5.4.0]undec-7-ene (141.5 gms) was added to the mixture at 50-55° C. Heated the mixture to 110-115° C. and stirred for 8 hours at the same temperature. Cooled the mixture to 25-30° C. Aqueous hydrochloric acid solution to the mixture at 25-30° C. Layers were separated and extracted the aqueous layer with toluene. Combined the organic layers and water was added. Layers were separated and washed the organic layer with aqueous sodium chloride solution. Distilled off the solvent completely from the organic layer under reduced pressure. To the obtained compound, methanol (100 ml) was added at 25-30° C. Cooled the reaction mixture to 0-5° C. and stirred for 2 hours at the same temperature. Filtered the precipitated solid and washed with pre-cooled methanol. To the obtained compound. Methanol (50 ml) was added at 25-30° C. Heated the reaction mixture to 60-65° C. and stirred for 20 minutes at the same temperature. Cooled the reaction mixture to 0-5° C. and stirred for 2 hours at the same temperature. Filtered the precipitated solid, washed with pre-cooled methanol and dried to get the title compound. Yield: 50 gms; Purity by HPLC: 99.24%.

Example-31: Preparation of methyl 3α-propionyloxy-6α-ethyl-7-keto-5β-cholan-24-oate Toluene (600 ml) was added to the compound obtained in example-29 at 25-30° C. and stirred for 15 minutes at the same temperature. Heated the mixture to 110-115° C. and stirred for 2 hours to remove the traces amount of water azeotropically from the mixture. Cooled the mixture to 50-55° C. 1,8-diazabicyclo[5.4.0]undec-7-ene (141.5 gms) was added to the mixture at 50-55° C. Heated the mixture to 110-115° C. and stirred for 8 hours at the same temperature. Cooled the mixture to 25-30° C. Water was added to the reaction mixture at 25-30° C. Layers were separated and extracted the aqueous layer with toluene. Combined the organic layers and water was added. Layers were separated and washed the organic layer with aqueous sodium chloride solution. Distilled off the solvent completely from the organic layer under reduced pressure. To the obtained compound, methanol (100 ml) was added at 25-30° C. Distilled off the solvent completely from the mixture under reduced pressure. Methanol was added to the obtained compound at 25-30° C. Cooled the reaction mixture to 0-5° C. and stirred for 2 hours at the same temperature. Filtered the precipitated solid and washed with pre-cooled methanol. To the obtained compound. Methanol (50 ml) was added at 25-30° C. Heated the reaction mixture to 60-65° C. and stirred for 20 minutes at the same temperature. Cooled the reaction mixture to 25-30° C. and further to 0-5° C. and stirred for 2 hours at the same temperature. Filtered the precipitated solid, washed with pre-cooled methanol and dried to get the title compound. Yield: 55 gms; M.R: 68-74° C. Purity by HPLC: 99.37%.

Example-32: Preparation of methyl 3α-propionyloxy-6α-ethyl-7α-hydroxy-5β-cholan-24-oate Methanol (140 ml) and tetrahydrofuran (140 ml) were added to methyl-3α-propionyloxy-6α-ethyl-7-keto-5β-cholanate (70.0 gms) at 25-30° C. Activated carbon (3.5) was added to the mixture at 25-30° C. Filtered the mixture through hyflow bed and washed the bed with tetrahydrofuran. Cooled the mixture to 0-5° C. Sodium borohydride (0.67 gms) was slowly added to the mixture in six lots at 0-5° C. and stirred for 4 hours at the same temperature. Acetic acid was slowly added to the mixture at 0-5° C. Raised the temperature of mixture to 25-30° C. Distilled off the solvent completely from the mixture under reduced pressure. Ethyl acetate (350 ml) was added to the mixture at 25-30° C. Aqueous sodium bicarbonate solution was added to the mixture at 25-30° C. Layers were separated and aqueous layer was extracted with ethyl acetate. Combined the total organic layers and added aqueous sodium chloride solution at 25-30° C. Layers were separated. Distilled off the solvent completely from the organic layer under reduced pressure to get title compound.
Yield: 70.0 gms; Purity by HPLC: 97.38%.

Example-33: Preparation of Obeticholic Acid Tertiary Butyl Amine Salt

Methanol (350 ml) was added to the compound obtained from example-32 at 25-30° C. Aqueous sodium hydroxide solution was added to the mixture at 25-30° C. Heated the mixture to 60-65° C. and stirred for 8 hours at same temperature. Distilled off the solvent completely from the mixture under reduced pressure. Water and ethyl acetate was added to the mixture at 25-30° C. Layers were separated and aqueous layer was extracted with ethyl acetate. Aqueous layer was cooled to 5-10° C. Aqueous hydrochloric acid was added to aqueous layer at 5-10° C. Ethyl acetate was added to the mixture at 5-10° C. Raised the temperature of the mixture to 25-30° C. and stirred for 30 minutes at same temperature. Layers were separated. Ethyl acetate was added to the aqueous layer at 25-30° C. Layers were separated. Combined the total organic layers and heated to 60-65° C. Tertiary butyl amine (10.21 gms) was slowly added to the mixture at 60-65° C. and stirred for 30 minutes at same temperature. Cooled the mixture to 25-30° C. and stirred for 90 minutes at the same temperature. Filtered the precipitated solid, washed with ethyl acetate and dried to get the title compound. Yield: 70 gms; Tertiary butyl amine content: 14.39%; Purity by HPLC: 99.91%.

Example-34: Preparation of Obeticholic Acid Tertiary Butyl Amine Salt

Methanol (350 ml) was added to the compound obtained from example-32 at 25-30° C. Aqueous sodium hydroxide solution was added to the mixture at 25-30° C. Heated the mixture to 60-65° C. and stirred for 8 hours at same temperature. Distilled off the solvent completely from the mixture under reduced pressure. Water and ethyl acetate was added to the mixture at 25-30° C. Layers were separated and aqueous layer was extracted with ethyl acetate. Toluene was added to aqueous layer at 25-30° C. and stirred for 30 minutes at the same temperature. Layers were separated.

Aqueous layer was cooled to 0-5° C. Aqueous hydrochloric acid was added to aqueous layer at 0-5° C. Ethyl acetate was added to the mixture at 0-5° C. Raised the temperature of the mixture to 25-30° C. and stirred for 30 minutes at same temperature. Layers were separated. Ethyl acetate was added to the aqueous layer at 25-30° C. Layers were separated. Combined the total organic layers and aqueous sodium chloride solution was added at 25-30° C. and stirred for 15 minutes at the same temperature. Layers were separated. Distilled off the solvent completely from the organic layer under reduced pressure. Ethyl acetate was added to the obtained compound at 25-30° C. Raised the temperature of the reaction mixture to 40-45° C. and stirred for 15 minutes at the same temperature. Tertiary butyl amine (10.21 gms) was slowly added to the mixture at 40-45° C. and stirred for 30 minutes at same temperature. Cooled the mixture to 25-30° C. and stirred for 60 minutes at the same temperature. Filtered the precipitated solid and washed with ethyl acetate. Dichloromethane was added to the obtained compound at 25-30° C. Cooled the reaction mixture to 0-5° C. and stirred for 45 minutes at the same temperature. Filtered the solid, washed with dichloromethane and dried to get the title compound. Purity by HPLC: 99.93%.

Example-35: Preparation of Amorphous Obeticholic Acid

Water (700 ml) was added to the compound obtained in example-34 at 25-30° C. Aqueous sodium hydroxide was added to the mixture at 25-30° C. and stirred for 2 hours under nitrogen atmosphere. Filtered the resulting mixture. Cooled the obtained filtrate to 5-10° C. Aqueous hydrochloric acid was added to the reaction mixture at 5-10° C. Raised the temperature of the reaction mixture to 25-30° C. and stirred for 1 hour at the same temperature. Filtered the precipitated solid. Water (700 ml) was added to the obtained compound at 25-30° C. Heated the reaction mixture to 40-45° C. and stirred for 45 minutes at the same temperature. Filtered the solid, washed with water and dried to get the title compound.
Yield: 40 gms; Purity by HPLC: 99.94%.
The PXRD pattern of the obtained compound is similar to the PXRD pattern of FIG. 10 disclosed in U.S. Pat. No. 9,238,673 B2.

Example-36: Preparation of Amorphous Obeticholic Acid

Water (1500 ml) was added to the compound obtained in example-34 at 25-30° C. Aqueous sodium hydroxide was added to the mixture at 25-30° C. Heated the reaction mixture to 40-45° C. and stirred for 30 minutes at the same temperature. Filtered the resulting mixture. Cooled the obtained filtrate to 0-5° C. Aqueous hydrochloric acid was added to the reaction mixture at 0-5° C. Raised the temperature of the reaction mixture to 25-30° C. and stirred for 1 hour at the same temperature. Filtered the precipitated solid. Water (700 ml) was added to the obtained compound at 25-30° C. Heated the reaction mixture to 40-45° C. and stirred for 45 minutes at the same temperature. Filtered the solid, washed with water and dried to get the title compound.
Yield: 68 gms.
Purity by HPLC: 99.95%; CDCA impurity: 0.04%; Isomer-I: Not detected; 3N Acid impurity: 0.02%; Isomer-2: Not detected; Triol impurity: 0.02%.
Particle Size Distribution (PSD): D(10) is 5.48 μm; D(50) is 15.69 μm; D(90) is 35.37 μm; D[4.3] is 18.41 μm.

The PXRD pattern of the obtained compound is similar to the PXRD pattern of FIG. 10 disclosed in U.S. Pat. No. 9,238,673 B2.

We claim:
1. A process for the preparation of Obeticholic acid

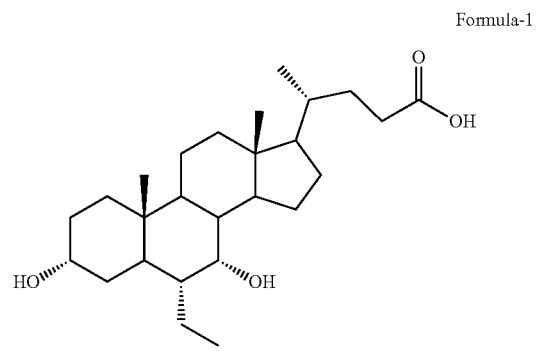 [SMILES: CC[C@@H]1C2C[C@H](O)CC[C@]2(C)C2CC[C@@]3(C)C(CCC3[C@H](C)CCC(=O)O)C2[C@@H]1O]

Formula-1 comprising:
a) reacting methyl 3α-hydroxy-6-ethylidene-7-keto-5β-cholan-24-oate compound of formula-14

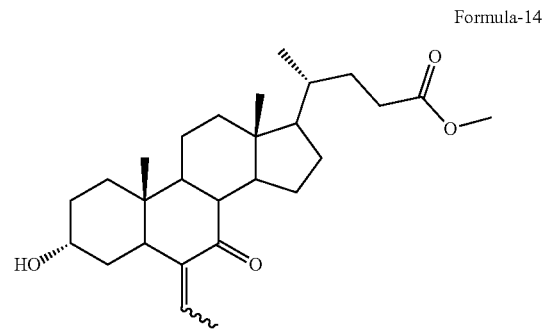

Formula-14 with a propionylating agent to provide methyl 3α-propionyloxy-6-ethylidene-7-keto-5β-cholan-24-oate compound of formula-15, and

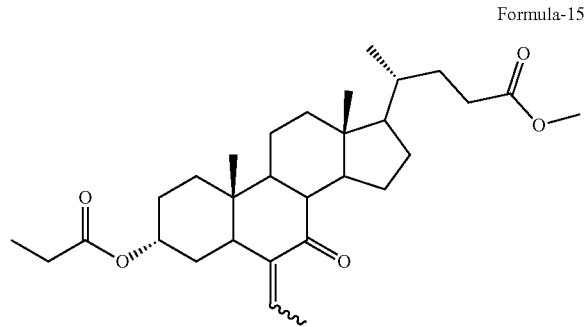

Formula-15 b) converting the compound of formula-15 to Obeticholic acid.

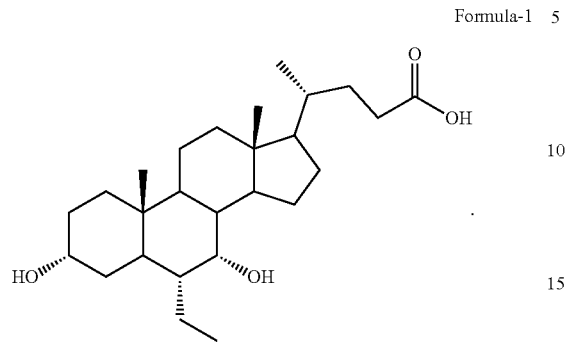
Formula-1

2. The process according to claim 1 wherein, in step-a) a base and optionally a solvent is used in the reaction therein.

3. The process according to claim 2 wherein, propionylating agent is selected from propionic anhydride or propionyl chloride; the base is selected from organic base or inorganic base; the solvent is selected from the group consisting of chloro solvents, acetic acid, alcohol solvents, ketone solvents, polar solvents, hydrocarbon solvents, nitrile solvents, ether solvents, ester solvents, polar-aprotic solvents, and a mixture thereof.

4. The process according to claim 1, further comprises:
a) reducing the compound of formula-15

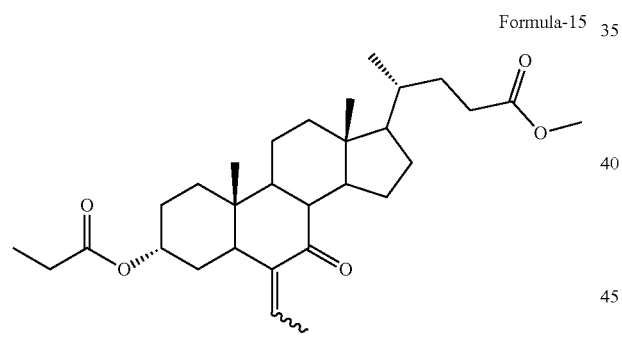
Formula-15 with a reducing agent to provide methyl 3α-propionyloxy-6-ethyl-7-keto-5β-cholan-24-oate compound of formula-16,

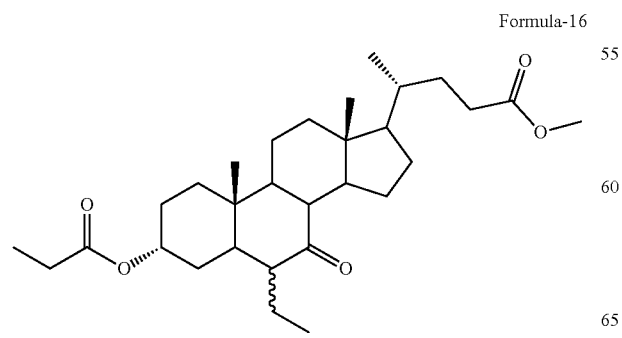
Formula-16 b) treating the compound of formula-16 with a base to provide methyl 3α-propionyloxy-6α-ethyl-7-keto-5β-cholan-24-oate compound of formula-17,

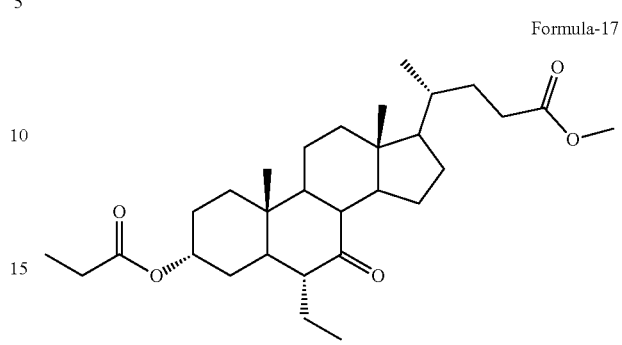
Formula-17 c) reducing the compound of formula-17 with a reducing agent to provide methyl 3α-propionyloxy-6α-ethyl-7α-hydroxy-5β-cholan-24-oate compound of formula-18, and

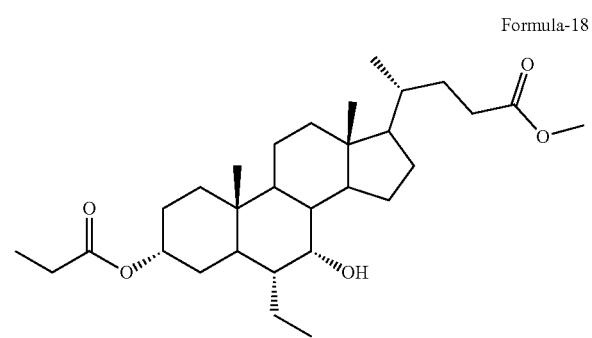 [SMILES: CCC(=O)O[C@@H]1CC[C@]2(C)C3CC[C@@]4(C)C(CCC4[C@H](C)CCC(=O)OC)C3[C@H](O)[C@H](CC)C2C1]
Formula-18 d) converting the compound of formula-18 to Obeticholic acid of formula-1.

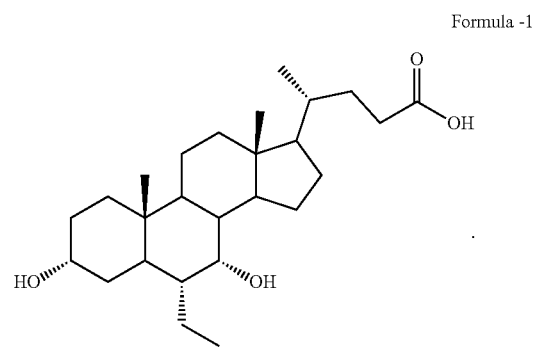 [SMILES: CC[C@@H]1C2C[C@H](O)CC[C@]2(C)C2CC[C@@]3(C)C(CCC3[C@H](C)CCC(=O)O)C2[C@@H]1O]
Formula-1

5. The process according to claim 4 wherein,
the suitable reducing agent used in step-a) is a transition metal catalyst selected from the group consisting of copper, nickel, palladium, platinum, rhodium, iridium, and ruthenium, in presence of hydrogen gas pressure;
the suitable base used in steps-c) and e) is selected from an organic or an inorganic base;
the suitable reducing agent used in step-c) is selected from the group consisting of sodium borohydride, potassium borohydride, sodium cyanoborohydride, tetramethylammonium borohydride, and sodium triacetoxyborohydride; and the suitable solvent used in step-a) to step-d) is selected from the group consisting of chloro solvents, alcohol solvents, ester solvents, ketone solvents, nitrile solvents, ether solvents, polar aprotic solvents, hydrocarbon solvents, polar solvents and a mixture thereof.

6. The process according to claim 1 wherein the compound of formula-15 is prepared by a process comprising:

a) reacting methyl 3α-hydroxy-7-keto-5β-cholanate compound of formula-2,

Formula-2

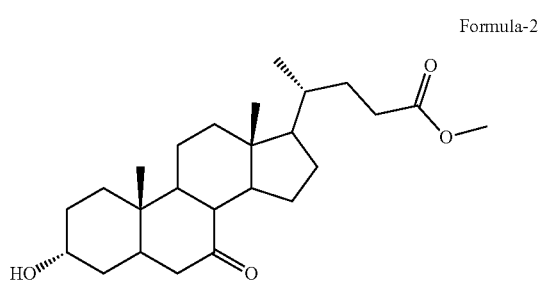 [SMILES: COC(=O)CC[C@@H](C)C1CCC2C3C(=O)CC4C[C@H](O)CC[C@]4(C)C3CC[C@@]21C]

with trimethylsilyl halide in the presence of a base to provide methyl 3α,7-di-trimethylsiloxy-6-en-5β-cholanate compound of formula-3, Formula-3

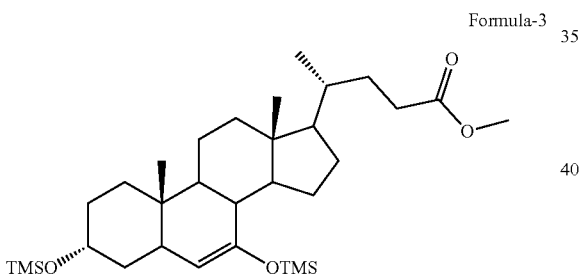

b) reacting compound of formula-3 with acetaldehyde in the presence of BF$_3$-etherate and a base in a solvent optionally in the presence of molecular sieves to provide 3α-hydroxy-6-ethylidene-7-keto-5β-cholan-24-oate compound of formula-14, and Formula-14

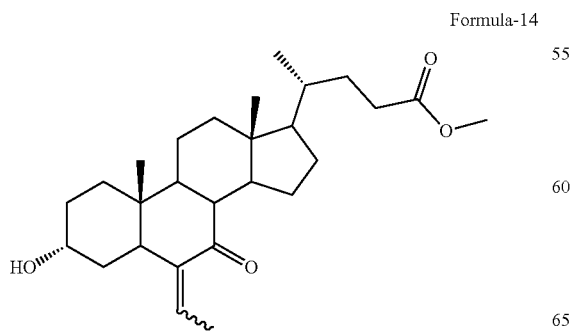

c) treating methyl 3α-hydroxy-6-ethylidene-7-keto-5β-cholan-24-oate compound of formula-14 with a propionylating agent in presence of a base and optionally in a solvent to provide methyl 3α-propionyloxy-6-ethylidene-7-keto-5β-cholan-24-oate compound of formula-15.

Formula-15

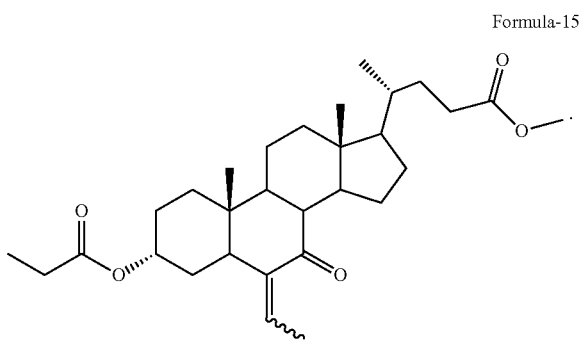

7. A process for the preparation of Obeticholic acid

Formula-1

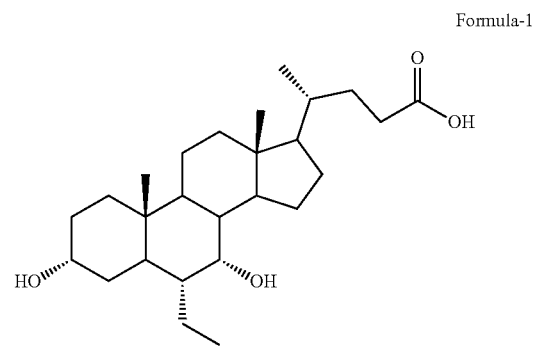 [SMILES: CC[C@@H]1C2C[C@H](O)CC[C@]2(C)C2CC[C@@]3(C)C(CCC3[C@H](C)CCC(=O)O)C2[C@@H]1O]

comprising:

a) reacting methyl 3α-hydroxy-6-ethylidene-7-keto-5β-cholan-24-oate compound of formula-14

Formula-14

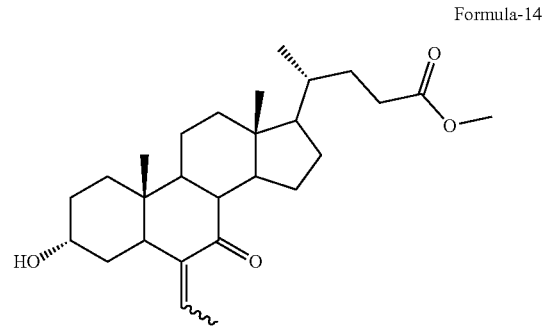

with a propionylating agent selected from propionic anhydride or propionyl chloride to provide methyl 3α-propionyloxy-6-ethylidene-7-keto-5β-cholan-24-oate compound of formula-15, and
b) converting the compound of formula-15 to Obeticholic acid.
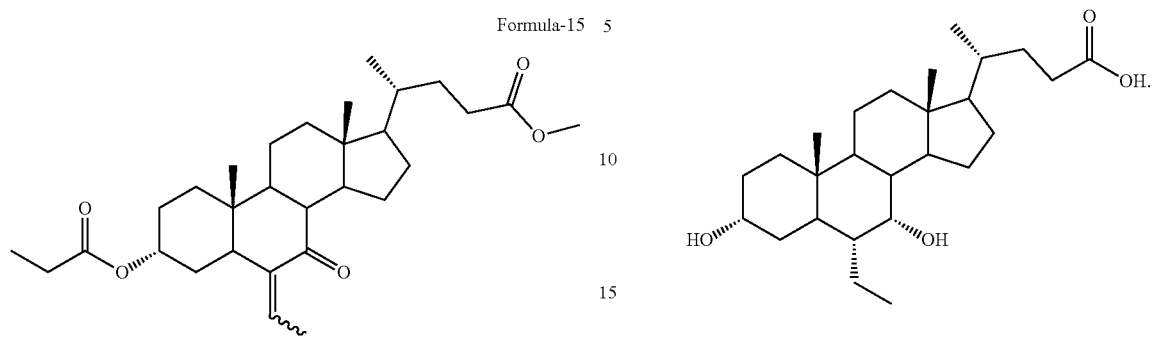
Formula-15
Formual-1
* * * * *